US009613438B2

(12) United States Patent
Takemoto et al.

(10) Patent No.: US 9,613,438 B2
(45) Date of Patent: Apr. 4, 2017

(54) X-RAY DIAGNOSTIC APPARATUS AND MEDICAL IMAGE PROCESSING METHOD

(71) Applicants: Toshiba Medical Systems Corporation, Otawara-shi (JP); THE RESEARCH FOUNDATION FOR THE STATE UNIVERSITY OF NEW YORK, Amherst, NY (US)

(72) Inventors: Hisato Takemoto, Amherst, MA (US); Amit Jain, Amherst, MA (US); Takuya Sakaguchi, Utsunomiya (JP); Stephen Rudin, Buffalo, NY (US); Daniel Bednarek, Buffalo, NY (US); Ciprian Nicolae Ionita, Buffalo, NY (US)

(73) Assignees: TOSHIBA MEDICAL SYSTEMS CORPORATION, Otawara-shi (JP); The Research Foundation for the State University of New York, Amherst, NY (US)

( * ) Notice: Subject to any disclaimer, the term of this patent is extended or adjusted under 35 U.S.C. 154(b) by 182 days.

(21) Appl. No.: 14/553,716

(22) Filed: Nov. 25, 2014

(65) Prior Publication Data

US 2016/0148398 A1    May 26, 2016

(51) Int. Cl.
| | |
|---|---|
| *G01N 23/04* | (2006.01) |
| *G06T 11/00* | (2006.01) |
| *A61B 6/00* | (2006.01) |
| *A61B 6/03* | (2006.01) |
| *A61B 6/08* | (2006.01) |

(52) U.S. Cl.
CPC ............ *G06T 11/005* (2013.01); *A61B 6/032* (2013.01); *A61B 6/08* (2013.01); *A61B 6/4266* (2013.01); *A61B 6/4441* (2013.01); *A61B 6/4452* (2013.01); *A61B 6/547* (2013.01); *A61B 6/585* (2013.01); *A61B 6/587* (2013.01); *A61B 6/5235* (2013.01); *A61B 6/5247* (2013.01); *A61B 6/5276* (2013.01); *A61B 6/584* (2013.01)

(58) Field of Classification Search
CPC ......... G06T 7/0012; G06T 2207/30004; G06F 19/321; G01N 23/04; G01N 23/08; G01N 23/083; A61B 6/032; A61B 6/504; A61B 6/4266; A61B 6/547; A61B 6/5205; A61B 6/5247; A61B 6/587; A61B 6/12; A61B 6/583; A61B 6/584; A61B 6/585; G03B 42/047
USPC ............... 378/62, 98.2, 98.8, 163, 164, 207; 382/128, 132
See application file for complete search history.

(56) References Cited

U.S. PATENT DOCUMENTS

| | | |
|---|---|---|
| 6,285,739 B1 | 9/2001 | Rudin et al. |
| 2011/0007873 A1 | 1/2011 | Rudin |

*Primary Examiner* — Jurie Yun
(74) *Attorney, Agent, or Firm* — Oblon, McClelland, Maier & Neustadt, L.L.P.

(57) ABSTRACT

An X ray diagnostic apparatus includes an X ray tube generating X rays, a first detector detecting the X rays, at least one second detector arranged in front of a first detection surface of the first detector and including a second detection surface narrower than the first detection surface and indicator points provided on a rear surface of the second detection surface, a projection data generation unit generating first projection data based on an output from the first detector, and a positional shift detection unit detecting a positional shift of the second detector relative to the first detector in accordance with an imaging direction by using the first projection data and a predetermined positional relationship between the points and detection elements in the second detector.

23 Claims, 13 Drawing Sheets

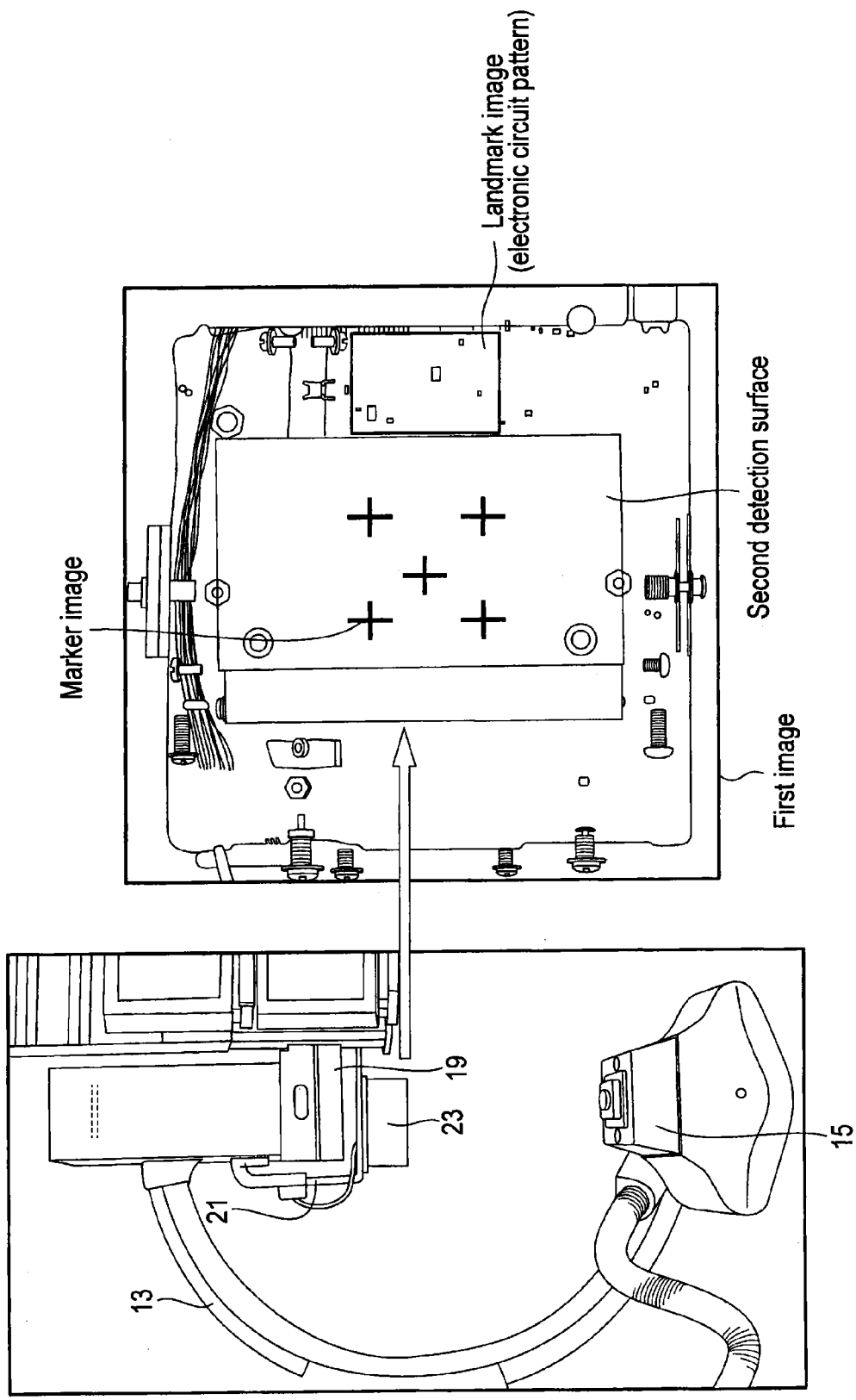
F I G. 2

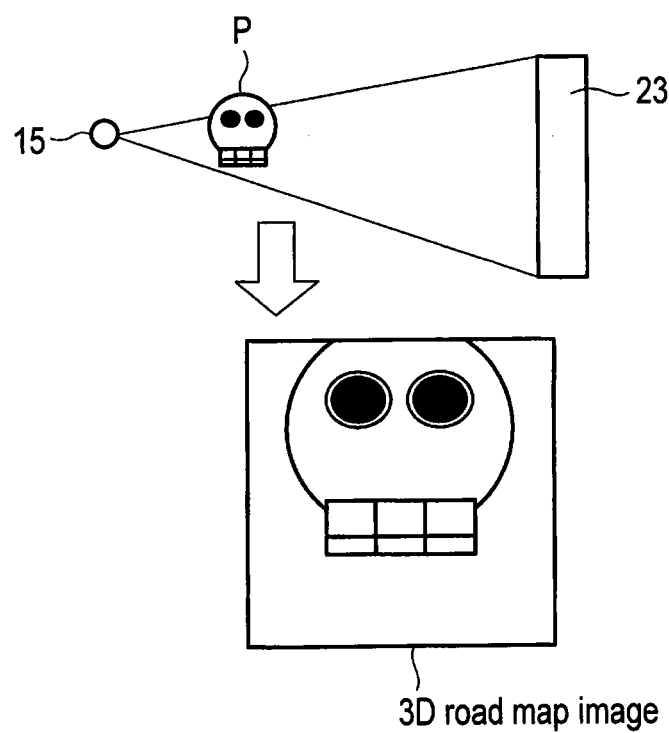
F I G. 8

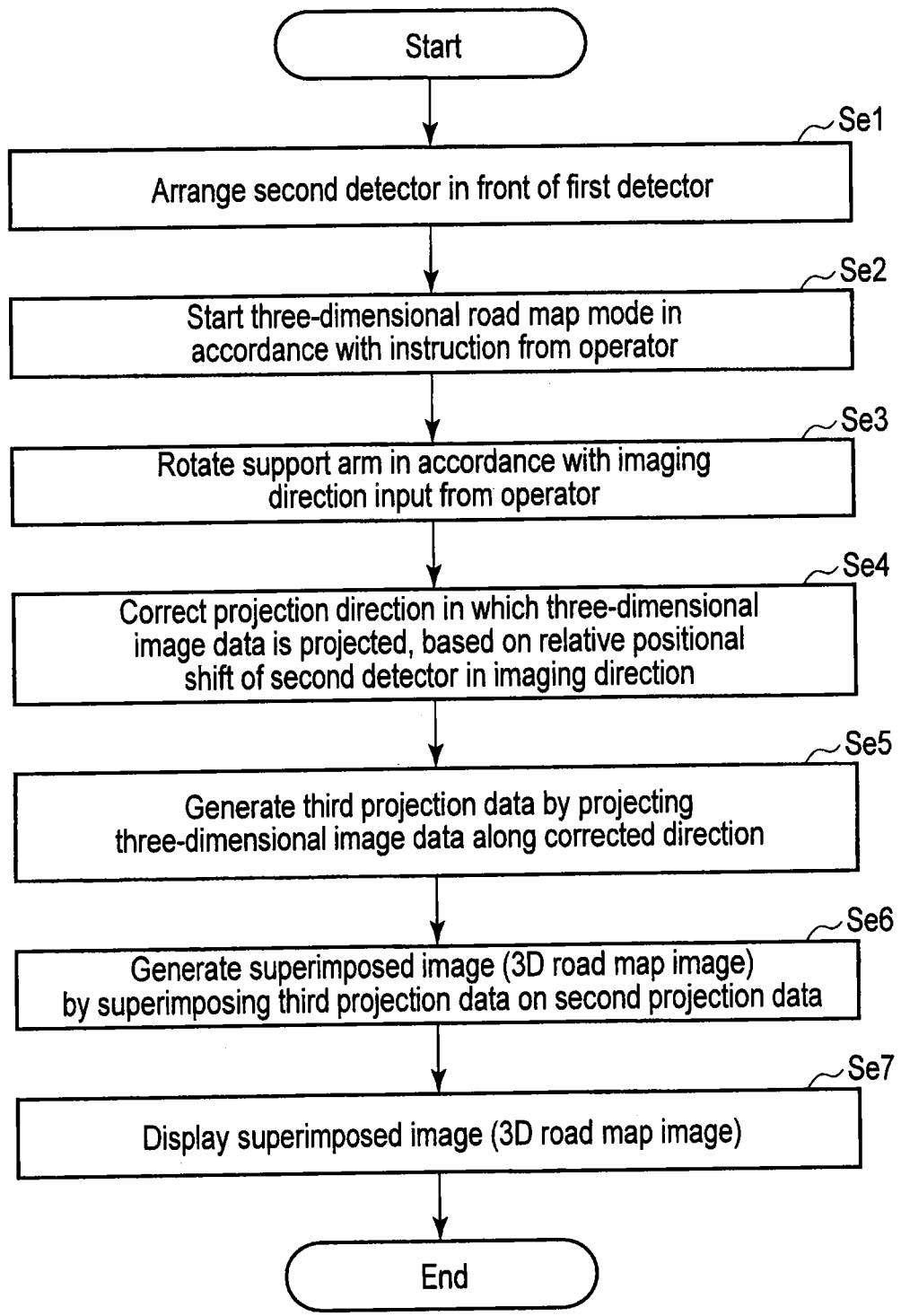
F I G. 9

X-RAY DIAGNOSTIC APPARATUS AND MEDICAL IMAGE PROCESSING METHOD

FIELD

Embodiments described herein relate generally to an X-ray diagnostic apparatus and a medical image processing method.

BACKGROUND

There has been proposed an X-ray diagnostic apparatus having a system (MAF (Micro Angiography Fluoroscope System)) in which, in front of a conventional flat panel detector (to be referred to as detector A hereinafter), another detector (to be referred to as detector B hereinafter) can be arranged. Detector A in the MAF system has a larger detection element size than detector B and/or a standard spatial resolution.

Detector B in the MAF system is arranged in front of detector A. Detector B in the MAF system has a smaller detection element size than detector A and/or a high spatial resolution. Detector B is attached to a C-arm through a holder mechanism. The holder mechanism supports detector B so as to make it movable between a park position and an X-ray irradiation range.

When acquiring a series of images while rotating the C-arm, it is necessary to correct the vibration of the C-arm and the incompleteness of the rotational orbit of the C-arm, in order to obtain an accurate three-dimensional reconstructed image. These corrections are achieved by the geometrical calibration of a detector. In a conventional angiography system, a calibration table used before reconstruction is generated from a series of images obtained by imaging a specific calibration phantom.

In the X-ray diagnostic apparatus having the MAF system, a holder supports detector B. In rotational imaging using detector B, therefore, sagging and vibration occur in detector B with respect to the original position of detector B. In a related art, the correction of the geometrical position of detector B has the following two problems.

First, the above calibration table is generated based on the assumption that the incompleteness of the rotational orbit of the C-arm and the vibration of the C-arm repeatedly occur each time. However, in an X-ray diagnostic apparatus having an MAF system, the features of the vibration of the C-arm (to be referred to as vibration characteristics hereinafter) change because of a change in the distribution of masses between detector B at the park position and detector B arranged in front of detector A. A change in the vibration characteristics of the C-arm breaks the assumption that the vibration characteristics of the C-arm are invariable when the vibration of the C-arm repeats and the C-arm rotates at two different positions relative to detector B. This poses a problem that the above calibration table is inappropriate for the correction of a geometrical position relative to detector B.

Second, since the visual field size of detector B is smaller than that of detector A, it is not appropriate to use, for detector B, the calibration phantom for the calibration of a geometrical position relative to detector A. In general, when using a calibration phantom, a detector having an appropriate size is required to generate image data with high accuracy and to cover the field of view.

However, detector B typically has a smaller field of view than detector A. For this reason, requiring a different calibration phantom for detector B will increase the manufacturing cost of an angiography system and increase the complexity of a calibration procedure. The use for detector B of a calibration table designed for detector A does not produce a satisfactory result in reconstruction using the projection data obtained by rotational angiography because of additional vibration of the holder caused by potential mechanical instability of the holder mechanism with respect to detector B.

That is, when reconstructing volume data based on an output from detector B in an X-ray diagnostic apparatus having an MAF system, the related art requires a phantom suitable for the visual field size of detector B to correct the geometrical deformation and vibration of the C-arm including a holder mechanism. In this case, since accuracy is required when manufacturing a phantom dedicated to detector B, the cost will increase. In addition, it takes much time to perform calibration for detector B.

Furthermore, if the angle of a C-arm with respect to the vertical axis is large (e.g., 90°), the sagging amount of detector B increases due to the influence of gravity. For example, as shown in FIG. 13, if the position of a collimator blade when the angle of the C-arm is 90° coincides with the position (FIG. 14) of the collimator blade when the angle of the C-arm is 0°, since the position of detector B moves in the vertical direction, the irradiation range of X-rays becomes inappropriate.

FIG. 13 shows a state in which detector B which is moved in front of detector A is arranged at a side surface (at a position of 90°) of an object (top plate). In this case, no X-rays are detected at the upper end portion of the detection surface of detector B because of the sagging of detector B. In addition, the sagging of detector B makes the collimator blade overlap the lower end portion of the detection surface of detector B, resulting in shielding X-rays. FIG. 14 shows a state in which detector B which is moved in front of detector A is arranged at the front surface (e.g., a position of (0°) of the object (top plate). In this case, the collimator properly limits the X-ray irradiation range.

As shown in FIG. 13, since those of the collimated X-rays which do not reach the X-ray detection surface of detector B are not visualized, the object is unnecessarily exposed to X-rays. In addition, in this case, since part of the collimator blade covers part of the X-ray irradiation range which corresponds to part of the detection surface of detector B, the detection surface of detector B cannot be effectively used. Furthermore, when using detector B in a very narrow visual field, the visual field desired by the operator may be blocked by the collimator blade.

Conventionally, a virtual projection image (e.g., a blood vessel image, an image similar to an X-ray image, or a three-dimensional road map image) is sometimes generated based on the geometrical information of a C-arm and an X-ray optical system (a tube focus and an FPD) and volume data acquired in advance (the three-dimensional image obtained by the C-arm, CT (Computed Tomography) volume data, MRI (Magnetic Resonance Imaging) volume data, or the like). The generated projection image is superimposed/displayed on an actually acquired X-ray image.

When acquiring an X-ray image, if the angle of the C-arm relative to the vertical axis is large (e.g., 90°), the sagging amount of detector B increases due to the influence of gravity. On the other hand, the object is placed on the top plate, and hence its position is invariable. For this reason, for example, as shown in FIG. 14, the X-ray irradiation range differs from the ideal irradiation range because of the sagging of detector B. On the other hand, the projection image generated based on the volume data acquired in advance is generated based on the ideal geometrical information of the C-arm and the X-ray optical system. For this reason, as shown in FIG. 15, this image shifts from the actually acquired X-ray image.

"A" in FIG. 15 indicates an ideal case without any sagging of detector B. In this case, when detector B which is moved in front of detector A is arranged at a side surface (a position of (90°) of the object, the X-ray irradiation range associated with the image obtained by detector B coincides with the virtual X-ray irradiation range associated with the projection image of volume data. That is, in an ideal case without any sagging of detector B, the positional relationship with the image obtained by detector B coincides with that of the projection image of the volume data.

"B" in FIG. 15 indicates a case with the sagging of detector B. In this case, when detector B which is moved in front of detector A is arranged at a side surface (a position of (90°) of the object, the X-ray irradiation range associated with the image obtained by detector B differs from the virtual X-ray irradiation range associated with the projection image of the volume data. That is, the positional relationship with the image obtained by detector B differs from that with the projection image of the volume data because of the sagging of detector B.

BRIEF DESCRIPTION OF THE DRAWINGS

FIG. 2 is a view showing an example of the second detector arranged at the front surface position and the first image according to the first embodiment;

FIG. 8 is a view showing an example of 3D road map image obtained by superimposing the third image generated by using a corrected projection direction on the second image according to the third embodiment;

FIG. 9 is a flowchart showing an example of a procedure for projection direction correction processing according to the third embodiment;

DETAILED DESCRIPTION

Figure 1:
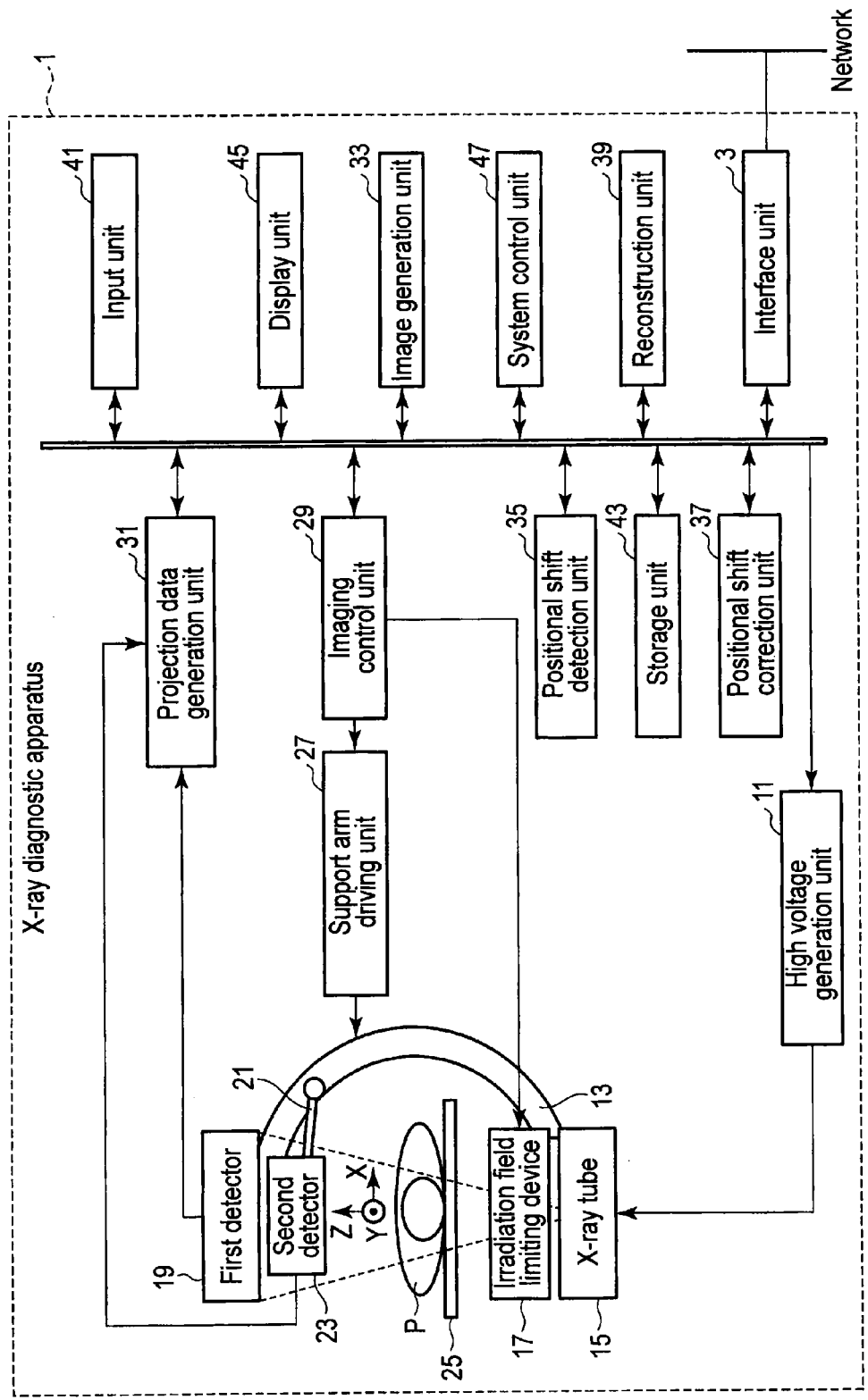
FIG. 1 is a block diagram showing an example of the arrangement of an X-ray diagnostic apparatus according to the first embodiment.

In general, according to one embodiment, an X-ray diagnostic apparatus includes an X-ray tube, a first detector, at least one second detector, a projection data generation unit, and a positional shift detection unit.

The X-ray tube generates X-rays. The first detector detects the X-rays. The at least one second detector is arranged in front of a first detection surface of the first detector. The second detector includes a second detection surface narrower than the first detection surface and indicator points provided on a rear surface of the second detection surface. The projection data generation unit generates first projection data based on an output from the first detector. The positional shift detection unit detects a positional shift of the second detector relative to the first detector in accordance with an imaging direction by using the first projection data and a predetermined positional relationship between the indicator points and a plurality of detection elements in the second detector.

An X-ray diagnostic apparatus according to the embodiment will be described below with reference to the accompanying drawings. Note that the same reference numerals in the following description denote constituent elements having almost the same functions and arrangements, and a repetitive description will be made only when required.

(First Embodiment)

FIG. 1 shows the arrangement of an X-ray diagnostic apparatus 1 according to the first embodiment. The X-ray diagnostic apparatus 1 includes an interface unit 3, a high voltage generation unit 11, a support arm 13, a bed 25, a support arm driving unit 27, an imaging control unit 29, a projection data generation unit 31, an image generation unit 33, a positional shift detection unit 35, a positional shift correction unit 37, a reconstruction unit 39, an input unit 41, a storage unit 43, a display unit 45, and a system control unit 47.

The interface unit 3 connects the X-ray diagnostic apparatus 1 to an electronic communication line (to be referred to as a network hereinafter). A radiology department information management system (not shown), a hospital information system (not shown), and the like are connected to the network.

The high voltage generation unit 11 generates a tube current to be supplied to an X-ray tube 15 and a tube voltage to be applied to the X-ray tube 15 under the control of the system control unit 47. The high voltage generation unit 11 supplies the generated tube current to the X-ray tube 15 and applies the generated tube voltage to the X-ray tube 15.

The support arm 13 supports the X-ray tube 15, a beam limiting device 17, a first detector 19, and a support mechanism 21. The support arm 13 is, for example, a C-arm. Note that the support arm 13 may be an Ω-arm instead of the C-arm. The C-arm is supported by a support unit (not shown) so as to be slidable in a direction (to be referred to as a C direction hereinafter) along the C shape of the C-arm. The support unit supports the C-arm so as to make it rotatable in a direction (to be referred to as a C orthogonal direction) orthogonal to the C direction almost centered on the support portion where the C-arm is supported. Note that the support unit can also support the C-arm so as to make it translatable in the short- and long-axis directions of the top plate.

The X-ray tube 15 generates X-rays at the tube focus based on the tube current supplied from the high voltage generation unit 11 and the tube voltage applied by the high voltage generation unit 11. The X-rays generated from the tube focus irradiate an object P through an X-ray radiation window provided in front of the X-ray tube 15.

The beam limiting device 17 is provided in front of the X-ray radiation window at the X-ray tube 15. That is, the beam limiting device 17 is provided between the X-ray tube 15 and the first detector 19. More specifically, the beam limiting device 17 limits the irradiation range with the maximum diameter (to be referred to as the maximum irradiation range hereinafter) in accordance with an irradiation area, on the body surface of the object P, which is irradiated with X-rays, in order to prevent portions other than an imaging region (X-ray irradiation region) desired by the operator from being exposed to the X-rays generated at the tube focus. For example, the beam limiting device 17 limits an irradiation range by moving each of a plurality of collimator blades (first and second collimator blades) in accordance with the irradiation range limiting instruction input from the input unit 41.

That is, the beam limiting device 17 limits the X-rays generated by the X-ray tube 15 to irradiate a region of the object desired by the operator (X-ray irradiation region). More specifically, the beam limiting device 17 includes a plurality of first collimator blades which can move in a predetermined direction and a plurality of second collimator blades which can move in a direction perpendicular to the predetermined direction. Each of the first and second collimator blades is formed from lead which shields X-rays generated at the tube focus. When imaging the second detector 23 (to be described after) arranged at a position at the front surface of the first detector 19, the first and second collimator blades of the beam limiting device 17 may be arranged at positions in the maximum irradiation range.

The first detector 19 detects the X-rays generated from the X-ray tube 15 and transmitted through the object P or phantom. The detection surface (to be referred to as the first detection surface hereinafter) of the first detector 19 is wider than the detection surface (to be referred to as the second detection surface hereinafter) of the second detector 23. In addition, the spatial resolution of the first detector 19 is lower than that of the second detector 23.

The first detector 19 is, for example, an FPD (Flat Panel Detector). The FPD includes a plurality of semiconductor detection elements (to be referred to as the first detection elements). The first detection element includes either a direct conversion type or an indirect conversion type. The direct conversion type is a form of directly converting incident X-rays into an electrical signal. The indirect conversion type is a form of converting incident X-rays into light through a phosphor and converting the light into an electrical signal.

The electrical signals generated by a plurality of semiconductor detection elements in associate with incidence of X-rays are output to an A/D converter (Analog to Digital converter) (not shown). The A/D converter converts an electrical signal into digital data. The A/D converter outputs the digital data to the projection data generation unit 31. Note that an image intensifier may be used as the first detector 19.

The support mechanism 21 supports at least one second detector 23 so as to make it movable between a position at the front surface (to be referred to as the front surface position hereinafter) of the first detector 19 and a park position. In this case, the park position is a position (retraction position) at which the second detector 23 is retracted at a position spaced apart from the X-ray irradiation range (field of view) associated with the first detector 19. That is, the second detector 23 arranged at the park position is excluded from the field of view associated with the first detector 19.

The support mechanism 21 moves the second detector 23 from the front surface position to the park position in accordance with the operation of the operator. In addition, the support mechanism 21 moves the second detector 23 from the park position to the front surface position in accordance with the operation of the operator. Note that the support mechanism 21 may move the second detector 23 from the front surface position to the park position or from the park position to the front surface position in accordance with the instruction issued by the operator via the input unit 41.

The second detector 23 is supported by the support mechanism 21 so as to be movable between the front surface position and the park position. The second detection surface is narrower than the first detection surface. That is, the area of the second detection surface is smaller than that of the first detection surface. The spatial resolution of the second detector 23 is larger than that of the first detector 19. For example, the size of each of the plurality of detection elements (to be referred to as the second detection elements hereinafter) of the second detector 23 is smaller than that of each of the first detection elements.

A plurality of indicator points (markers) may be preferably provided on the rear surface side of the second detector 23, i.e., the surface, of the second detector 23 arranged at the front surface position, which directly faces the first detector 19. Each of the plurality of markers is formed from a material which highly attenuates X-rays (e.g., tungsten or lead; to be referred to as a radiopaque material hereinafter). Note that markers may be formed from beads made of a radiopaque material. In addition, a marker may be formed from a highly radiolucent pattern, such as a pattern having a hole structure. This pattern becomes a characteristic pattern formed from transmitting and non-transmitting regions.

The rear surface side of markers on the second detector 23 can transmit X-rays. That is, a radiopaque components (e.g., a power supply circuit and a lead shield) are not provided on the rear surface side of the markers on the second detector 23. Note that each marker has an arbitrary pattern shape (e.g., a "+" shape, Δ shape, or rectangular shape). In addition, the markers may be provided on the rear surface side of the second detector 23 so as to have a predetermined positional relationship with respect to the second detector's elements. The predetermined positional relationship is the relationship between the positions of the indicator points and the positions of the second detector's elements (or the pixels of the second image (to be described later)). The predetermined positional relationship is stored in the storage unit 43.

The second detector 23 arranged at the front surface position detects the X-rays transmitted through the object P. The second detector 23 is, for example, an FPD. The electrical signal generated in associate with incidence of X-rays on the second detector 23 is output from the second detector 23 to the A/D converter to be converted into digital data. The A/D converter outputs the digital data to the projection data generation unit 31.

The bed 25 has a top plate on which the object P or phantom is placed.

The support arm driving unit 27 drives the support arm 13 under the control of the imaging control unit 29. More specifically, the support arm driving unit 27 slides the support arm 13 in the C direction and rotates it in the C orthogonal direction by outputting a driving signal to the support arm 13 in accordance with a control signal from the imaging control unit 29.

For example, upon receiving an instruction via the input unit 41 for executing a rotational imaging of X ray imaging while rotating the support arm 13 around a predetermined rotation axis, the support arm driving unit 27 drives the support arm 13 to rotate it along a predetermined orbit around the rotation axis. In this case, the predetermined rotation axis is, for example, a straight line parallel to the mount surface of the top plate. In addition, the predetermined orbit is, for example, a circular orbit. Note that the support arm driving unit 27 may drive the support arm 13 under the control of the system control unit 47.

The imaging control unit 29 includes a CPU (Central Processing Unit) and a memory (neither of which is shown). The imaging control unit 29 controls the support arm 13, the beam limiting device 17, the bed 25, and the like in accordance with each type of imaging and an instruction from the system control unit 47.

For example, the imaging control unit 29 controls the support arm driving unit 27 to execute rotational imaging with respect to a helical phantom having helically arranged beads while the second detector 23 is arranged at the park position. This rotational imaging generates a correspondence table (to be referred to as the first correspondence table hereinafter) for correcting the orbit shift between the rotational orbit of the first detector 19 and the ideal rotational orbit in rotational imaging. The first correspondence table is a correspondence table which indicates correction of an orbit shift with respect to the imaging direction in rotational imaging. The first correspondence table is stored in the storage unit 43.

The imaging control unit 29 controls the support arm driving unit 27 to execute rotational imaging while the second detector 23 is arranged at the front surface position after the execution of rotational imaging with respect to the helical phantom. After the execution of this rotational imaging, the imaging control unit 29 controls the support arm driving unit 27 to execute rotational imaging with respect to the second detector 23 arranged at the front surface position by using the first detector 19. The imaging control unit 29 executes the above rotational imaging while maintaining a field of view covering a region which covers the second detection surface and is narrower than the first detection surface.

The imaging control unit 29 controls the support arm driving unit 27 to execute rotational imaging (to be referred to as object imaging hereinafter) with respect to the object (patient) placed on the top plate of the bed 25 after the execution of the above various types of rotational imaging.

Note that the imaging control unit 29 executes object imaging while maintaining a field of view corresponding to the second detection surface.

The projection data generation unit 31 executes preprocessing for the digital data output from the first detector 19 in association with rotational imaging. The projection data generation unit 31 executes preprocessing for the digital data output from the second detector 23 in association with object imaging. Preprocessing includes correction of sensitivity unevenness between the channels in the first X-ray detector 19 and the second X-ray detector 23 and correction concerning an excessive decrease in signal level or data omission due to an X-ray strong absorber such as a metal.

With the above preprocessing, the projection data generation unit 31 generates the first projection data corresponding to an output from the first detector 19 and the second projection data corresponding to an output from the second detector 23. The projection data generation unit 31 outputs the first projection data to the image generation unit 33, the positional shift detection unit 35, the positional shift correction unit 37, the storage unit 43, and the like. The projection data generation unit 31 outputs the second projection data to the image generation unit 33, the positional shift correction unit 37, the storage unit 43, and the like.

Note that the projection data generation unit 31 may select the second projection data to be used for the reconstruction of volume data in accordance with an instruction from the operator. At this time, the projection data generation unit 31 outputs the selected second projection data to the image generation unit 33, the positional shift correction unit 37, the storage unit 43, and the like.

The first projection data is projection data concerning the second detector 23 arranged at the front surface position. At this time, the first projection data includes the projection data of markers or a landmark. A landmark is a structure which may be attached or part of the second detector 23 and highly attenuates X-rays. This structure includes, for example, an electronic circuit and the edges, screws, and the like of the second detector 23. Note that the structure may form a bright point like a hole pattern which hardly attenuates X-rays.

The image generation unit 33 generates the first image based on the first projection data. The first image is an image concerning the second detector 23 arranged at the front surface position. At this time, the first image (indicator point image) includes a projection image of markers or landmark. Note that the image generation unit 33 may generate the second image based on the second projection data. The image generation unit 33 outputs the first and second images to the positional shift detection unit 35. The image generation unit 33 generates a medical image, which can be displayed on the display unit 45, by predetermined image processing based on the volume data reconstructed by the reconstruction unit 39. The predetermined image processing includes rendering processing and multiplanar reconstruction processing.

FIG. 2 is a view showing the second detector 23 arranged at the front surface position and an example of the first image. As shown in FIG. 2, the first image has a projection image of the second detector 23. The first image includes at least one of a projection image (marker image) of "+"-shaped markers provided on at least one of the rear surface of the second detection surface and the sides, and a projection image (landmark image) of a landmark corresponding to a structure (electronic circuit pattern) of the second detector 23.

The positional shift detection unit 35 detects the positional shift of the second detector 23 relative to the first detector 19 in rotational imaging in accordance with an imaging direction by using the first projection data and a predetermined positional relationship. The positional shift detection unit 35 outputs the detected relative positional shift to the positional shift correction unit 37. In the following description, an explanation concerning markers may also apply to a landmark.

More specifically, the positional shift detection unit 35 detects the position of a marker (to be referred to as the first marker position hereinafter) of the first projection data in each of a plurality of imaging directions φ in rotational imaging. The positional shift detection unit 35 specifies the position of a marker (to be referred to as the second marker position hereinafter) on the second detection surface. The positional shift detection unit 35 detects a relative positional shift based on the first and second marker positions.

Note that the positional shift detection unit 35 may detect a relative positional shift by using the first and second images. More specifically, the positional shift detection unit 35 detects the positional shift of the second detector 23 relative to the first detector 19 based on the first marker position on the first image and the second marker position on the second image in each of the plurality of imaging directions φ in rotational imaging. At this time, the second marker position is set in advance so as to satisfy a predetermined positional relationship with a pixel position on the second image.

Note that the predetermined positional relationship may be decided by the following calibration executed at a stage prior to the detection of a relative positional shift. In this calibration (to be referred to as pre-calibration hereinafter), the first image (first projection data) and the second image (second projection data) are generated by imaging the same object in rotational imaging. At this time, the first image includes a projection image of the object and a projection image of a marker. The second image includes a projection image of the object. In this case, the object is a phantom in which a plurality of beads which do not transmit X-rays are embedded. Performing pre-calibration can calibrate the relationship between a pixel on the second image and a marker position set on the second detector 23.

More specifically, the positional shift detection unit 35 specifies the positional relationship (to be referred to as the first positional relationship hereinafter) between a marker position and a bead position based on a pixel of a projection image of the marker and a pixel of a projection image of the bead in the first image. The positional shift detection unit 35 then detects the position of the bead on the second image. The positional shift detection unit 35 specifies a pixel on the second image which corresponds to the detected bead position. The positional shift detection unit 35 specifies a positional relationship (to be referred to as the second positional relationship) between the pixel specified on the second image and the bead position. The positional shift detection unit 35 decides the predetermined positional relationship between the marker and the pixel position of the marker based on the first positional relationship and the second positional relationship.

That is, the positional shift detection unit 35 can associate the pixel on the second image with the marker based on the first positional relationship and the second positional relationship. Pre-calibration concerning the position of a marker may be performed, for example, once in the process of manufacturing the X-ray diagnostic apparatus 1. Note that beads on the first and second images may be detected in accordance with the instruction issued by the operator via the input unit 41. In addition, in order to improve bead detection accuracy, the following processing may be executed. First of all, after the centers of a plurality of beads are designated in accordance with an instruction from the operator, binarization processing is executed with respect to the first and second images with a predetermined pixel value being a threshold. The center of gravity of a circular portion corresponding to a bead is then decided as the center of the bead, i.e., the position of the bead, on each of the first and second images having undergone binarization processing.

Note that as the positional shift of the second detector 23 relative to the first detector 19, it is possible to search for the pixel position of the second detector 23 on the first image by alignment between the first image and a template image in each of the plurality of imaging direction φ in rotational imaging. The above alignment processing is, for example, cross-correlation or template matching. In this case, a template image is an image obtained by imaging the second detector 23 using the first detector 19 in the manufacturing process for the X-ray diagnostic apparatus 1. Note that if a marker provided on the second detector 23 is a bead or the like, a template image may be generated by a predetermined calculation (simulation) based on conditions such as the size of the marker and image signal intensity originating from the marker. The template image is stored in the storage unit 43. The template image includes a projection image of a marker, circuit portion, or the like of the second detector 23.

More specifically, the positional shift detection unit 35 executes template matching processing by using the first image and the template image in each of a plurality of imaging directions. The positional shift detection unit 35 detects the positional shift of the second detector 23 relative to the first detector 19 in each imaging direction based on the template matching processing result. Note that the template matching processing may use, as prior information in advance, a region where a marker is very likely to exist (to be referred to as a marker existing region hereinafter).

This prior information makes it possible to intensively search the marker existing region for a marker, and hence can shorten the search time for a marker and improve the marker detection accuracy. Note that it is possible to use cross-correlation processing of calculating the cross-correlation between the first image and the template image instead of the above template matching processing. The positional shift detection unit 35 then detects a relative positional shift by applying various types of alignment processing such as pattern matching to the first and second images in each imaging direction (rotational angle).

The positional shift correction unit 37 generates a correction table (to be referred to as the second correspondence table hereinafter) for correcting a relative positional shift in each of the plurality of imaging directions φ based on the positional shift of the second detector 23 relative to the first detector 19. The second correspondence table is a table for defining the correction amount of the positional shift of a pixel position on the second detector 23 relative to the first detector 19.

More specifically, the positional shift correction unit 37 calculates an origin moving vector $V_\phi(V_X, V_Y)$ indicating the translation amount of the origin (to be referred to as the second origin hereinafter) of the second detector 23 with respect to the origin (to be referred to as the first origin hereinafter) of the first detector 19 in each of the plurality of imaging directions φ by using the relative positional shift in each of the plurality of imaging directions φ in rotational imaging. In this case, $V_X$ represents the translation amount of the second origin along the X direction of the first detector 19, and $V_Y$ represents the translation amount of the second origin along the Y direction perpendicular to the X direction.

When relative positional shifts are detected by using a plurality of markers, the positional shift correction unit 37 calculates a rotational angle $\theta_\phi$ of the second origin with respect to the first origin by using the relative positional shift in each of the plurality of imaging directions $\phi$. The positional shift correction unit 37 calculates a rotation matrix $R_\phi$ for the rotation of the position (x, y) of a pixel on the second detector 23 in each imaging direction $\phi$ by using the rotational angle $\theta_\phi$. The rotation matrix $R_\phi$ can be expressed by, for example, $$R_\phi = \begin{pmatrix} \cos\theta_\phi & \sin\theta_\phi \\ -\sin\theta_\phi & \cos\theta_\phi \end{pmatrix}$$

The positional shift correction unit 37 reads out, from the storage unit 43, the enlargement ratio of the second detection surface when projecting the second detection surface onto the first detection surface using X-rays. The enlargement ratio is calculated from, for example, the distance (to be referred to as SID (Source Image Distance)$_1$ hereinafter) between the first detector 19 and the radiation source and the distance (to be referred to as SID$_2$ hereinafter) between the second detector 23 and the radiation source. More specifically, an enlargement ratio M(x, y) is calculated as the ratio of SID$_1$(x, y) to SID$_2$(x, y) (M(x, y)=SID$_1$(x, y)/SID$_2$(x, y)).

The positional shift correction unit 37 generates the second correspondence table by using origin moving vector $V_\phi(V_X, V_Y)$) the rotation matrix $R_\phi$, and the enlargement ratio M(x, y). More specifically, the positional shift correction unit 37 calculates $P_1(X, Y)=R_\phi(P_2(x, y)\times M(x, y))+V_\phi$, where $P_1(X, Y)$ is a coordinate point (the position of the pixel on the first detector 19) after correction and $P_2(x, y)$ is the position of the pixel on the second detector 23. The positional shift correction unit 37 generates the second correspondence table indicating the coordinate point $P_1(X, Y)$ after correction which correspond to the imaging direction $\phi$ and the position $P_2(x, y)$ of the pixel on the second detector 23. The positional shift correction unit 37 may output the generated second correspondence table to the storage unit 43.

The positional shift correction unit 37 may decide, based on a relative positional shift, correction amounts by which the three-dimensional rotation and translation of the second detector 23 relative to the first detector 19 are corrected. At this time, this correction amount is incorporated in the second correspondence table. More specifically, the rotation matrix $R_\phi$ becomes a 3×3 three-dimensional rotation matrix, and the origin moving vector $V_\phi$ becomes a three-dimensional origin moving vector.

The positional shift correction unit 37 corrects a relative positional shift by using the second correspondence table with respect to the second projection data as a reconstruction target. This correction corrects the relative positional shift of the second projection data, and maps the resultant data on the first detection surface. The second projection data whose relative positional shift is corrected is mapped in a three-dimensional space in accordance with the first correspondence table, thereby correcting an orbit shift. The second projection data whose relative positional shift and orbit shift have been corrected (to be referred to as corrected projection data hereinafter) is output to the reconstruction unit 39.

Note that if the second correspondence table does not include the imaging direction of the second projection data, the positional shift correction unit 37 may decide a correction amount concerning the correction of a relative positional shift based on correction amounts (the rotation matrix $R_\phi$ and the origin moving vector $V_\phi$) concerning two imaging directions in the second correspondence table which are adjacent to the imaging direction of the second projection data. For the sake of simplicity, assume that the imaging direction of the second projection data is represented by $\phi_b$.

The positional shift correction unit 37 specifies two imaging directions $\phi_a$ and $\phi_c$ adjacent to $\phi_b$ in the second correspondence table. Not only two adjacent directions but also more than two adjacent directions may be used. The positional shift correction unit 37 calculates an origin moving vector $V_{\phi b}$ corresponding to $\phi_b$ by interpolation using the origin moving vectors $V_{\phi a}$ and $V_{\phi c}$ respectively corresponding to the specified imaging directions $\phi_a$ and $\phi_c$. The positional shift correction unit 37 calculates a rotational angle $\theta_{\phi b}$ corresponding to $\phi_b$ by interpolation using rotational angles $\theta_{\phi a}$ and $\theta_{\phi c}$ respectively corresponding to the specified imaging directions $\phi_a$ and $\phi_c$. The positional shift correction unit 37 calculates a rotation matrix $R_{\phi b}$ by using the calculated rotational angle $\theta_{\phi b}$. The positional shift correction unit 37 corrects a positional shift concerning the imaging direction $\phi_b$ of the second projection data by using the origin moving vector $V_{\phi b}$, the rotation matrix $R_{\phi b}$, and enlargement ratio M(x, y) according to $P_1(X, Y)=R_{\phi b}(P_2(x, y)\times M(x, y))+V_{\phi b}$.

The reconstruction unit 39 reconstructs volume data based on the corrected projection data obtained by correcting the relative positional shift and the orbit shift. For the sake of simplicity, a set of corrected projection data throughout all the channels in the same projection direction which are almost simultaneously acquired by one shot will be referred to as a corrected projection data set.

More specifically, the reconstruction unit 39 reconstructs a three-dimensional image (volume data) having an almost cylindrical shape with projection directions (view angles) falling within the range of 360° or 180°+fan angle by the Feldkamp method or sequential reconstruction method. The reconstruction unit 39 outputs the reconstructed volume data to the image generation unit 33.

The input unit 41 inputs various types of instructions, commands, information, selections, and settings from the operator to the X-ray diagnostic apparatus 1. For example, the input unit 41 inputs X-ray conditions, a rotational imaging position, an irradiation range, an instruction to move the second detector 23, a rotational imaging instruction, an object imaging instruction, an instruction to specify a bead, and the like. The input unit 41 includes a trackball, switch buttons, a mouse, and a keyboard (none of which are shown) which are used to make various types of settings.

The input unit 41 detects the coordinates of the cursor displayed on the display screen and outputs the detected coordinates to the system control unit 47. Note that the input unit 41 may be a touch panel provided to cover the display screen. In this case, the input unit 41 detects touched and designated coordinates by a coordinate reading principle such as an electromagnetic induction scheme, magnetostriction scheme, or a pressure-sensitive scheme, and outputs the detected coordinates to the system control unit 47.

The storage unit 43 stores various types of projection data generated by the projection data generation unit 31, various types of images generated by the image generation unit 33, the volume data reconstructed by the reconstruction unit 39, a predetermined positional relationship, the first correspondence table, the second correspondence table, a template image, the enlargement ratio M(x, y), and the like. The storage unit 43 stores control programs for the X-ray diagnostic apparatus 1, a diagnosis protocol, the operator's instructions sent from the input unit 41, various types of data groups such as X-ray conditions, various types of data sent via the interface unit 3 and a network, and the like.

The storage unit 43 stores reconstruction programs concerning various types of reconstruction methods used by the reconstruction unit 39, image processing programs concerning various types of image processing used by the image generation unit 33, a positional shift detection program for detecting a positional shift, a positional shift correction program concerning positional shift correction, and the like. Note that the storage unit 43 may store a medical image processing program which includes a positional shift detection program and a positional shift correction program and reconstructs corrected second projection data.

The display unit 45 includes a monitor which displays various types of medical images generated by the image generation unit 33, the input items (X-ray conditions, an irradiation range, an imaging position, and an imaging range) input from the input unit 41, and the like. The monitor displays the above various types of medical images, input items, and the like.

The system control unit 47 includes a CPU and a memory. The system control unit 47 temporarily stores, in the memory, information such as the operator's instructions sent from the input unit 41 and X-ray conditions such as imaging conditions. The system control unit 47 controls the respective units including the high voltage generation unit 11 and the imaging control unit 29 to execute rotational imaging and object imaging in accordance with the operator's instructions, X-ray conditions, and the like stored in the memory.

The system control unit 47 reads out various types of programs stored in the storage unit 43 and loads them to the memory. The system control unit 47 controls the respective units including the image generation unit 33, the positional shift detection unit 35, the positional shift correction unit 37, and the reconstruction unit 39 in accordance with the programs loaded to the memory.

(Positional Shift Correction Reconstruction Function)

The positional shift correction reconstruction function is a function of executing positional shift correction for the second detector 23 relative to the first detector 19 and orbit shift correction for the first detector 19 with respect to the second projection data and reconstructing volume data based on the corrected second projection data. Processing associated with the positional shift correction reconstruction function (to be referred to as positional shift correction reconstruction processing hereinafter) will be described.

Figure 3:
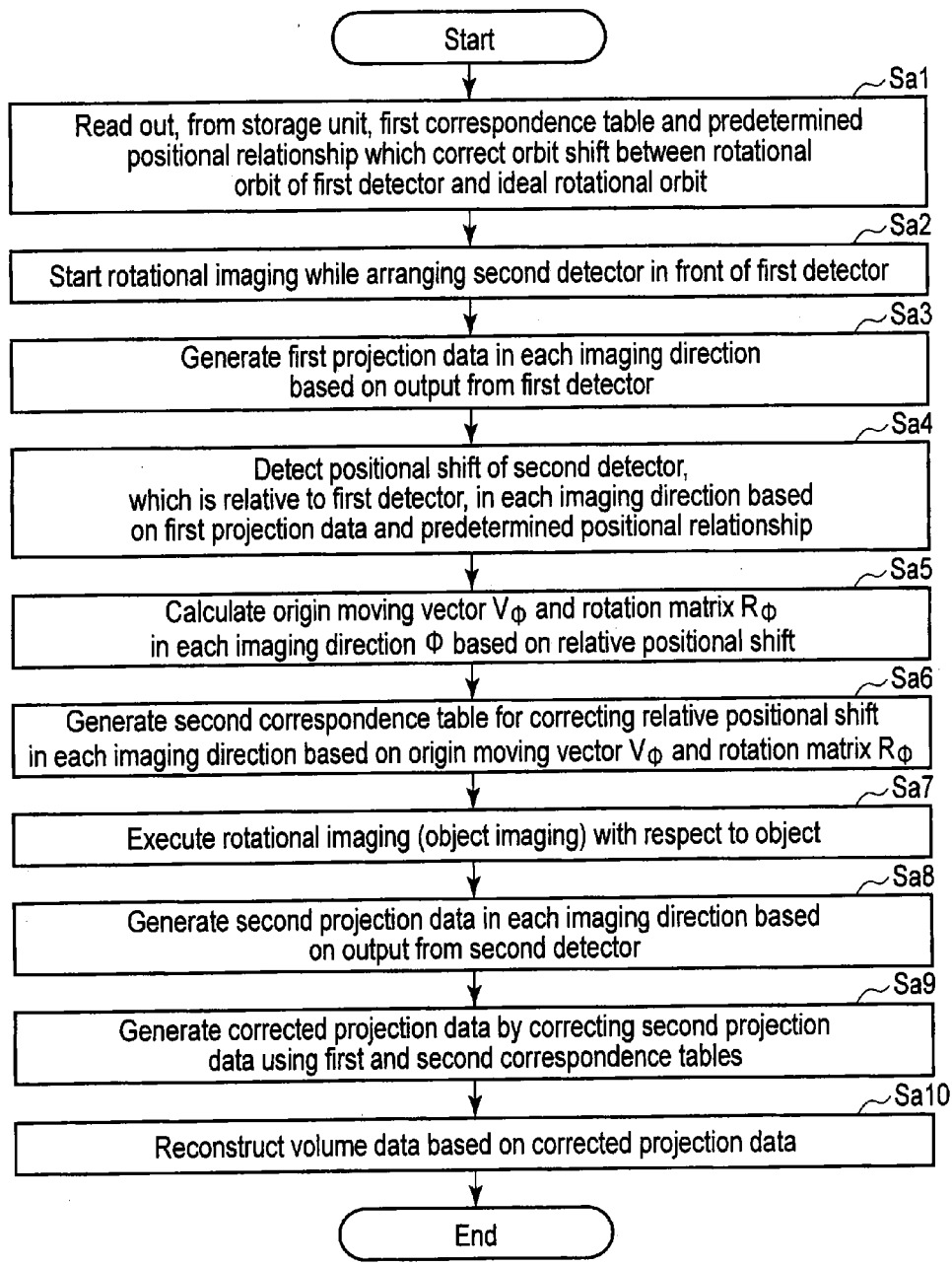
FIG. 3 is a flowchart showing an example of a procedure for positional shift correction reconstruction processing according to the first embodiment.

FIG. 3 is a flowchart showing an example of a procedure for positional shift correction reconstruction processing. In positional shift correction reconstruction processing, rotational imaging is executed before object imaging to detect the positional shift of the second detector 23 relative to the first detector 19.

The first correspondence table for correcting the orbit shift between the rotational orbit of the first detector 19 and the ideal rotational orbit and a predetermined positional relationship are read out from the storage unit 43 (step Sa1). The first correspondence table and the predetermined positional relationship are generated before the detection of the positional shift of the second detector 23 relative to the first detector 19. The second detector 23 is arranged in front of the first detector 19, and rotational imaging is started (step Sa2). At this time, the second detector 23 is imaged by the first detector 19. The first projection data associated with the second detector 23 is generated based on an output from the first detector 19 (step Sa3).

A relative positional shift in each imaging direction is detected based on the first projection data and the predetermined positional relationship (step Sa4). The origin moving vector $V_\phi$ and the rotation matrix $R_\phi$ are calculated in each imaging direction $\phi$ based on the relative positional shift (step Sa5). The second correspondence table for correcting the relative positional shift is generated based on the origin moving vector $V_\phi$ and the rotation matrix $R_\phi$ (step Sa6). The second correspondence table is stored in the storage unit 43.

Rotational imaging (object imaging) is executed for the object (step Sa7). The second projection data is generated in each imaging direction based on an output from the second detector 23 (step Sa8). Corrected projection data is generated by correcting the second projection data based on the first and second correspondence tables (step Sa9). Volume data is reconstructed based on the corrected projection data (step Sa10).

(First Modification)

A difference from the first embodiment is that no marker is provided on the rear surface of the second detector 23. In this case, this X-ray diagnostic apparatus detects a relative positional shift in the following manner.

The imaging control unit 29 controls the support arm driving unit 27 to execute the first rotational imaging (to be referred to as the first imaging hereinafter) with respect to a predetermined object upon arranging the second detector 23 at the park position. The predetermined object is a three-dimensional asymmetrical object which attenuates X-rays, for example, a rounded wire. The imaging control unit 29 then controls the support arm driving unit 27 to execute rotational imaging (to be referred to as the second imaging hereinafter) with respect to the predetermined object upon arranging the second detector 23 at the front surface position.

Note that the imaging control unit 29 controls the support arm driving unit 27, the high voltage generation unit 11, and the like to image the object in the same imaging direction and under the same imaging conditions in the first imaging and the second imaging. The imaging control unit 29 controls the support arm driving unit 27, the high voltage generation unit 11, and the like to execute object imaging after the execution of the first imaging and the second imaging.

The projection data generation unit 31 generates projection data (to be referred to as the first obtained projection data hereinafter) based on an output from the first detector 19 in the first imaging. The projection data generation unit 31 generates projection data (to be referred to as the second obtained projection data hereinafter) based on an output from the second detector 23 in the second imaging. The projection data generation unit 31 outputs the first obtained projection data and the second obtained projection data to the image generation unit 33.

The image generation unit 33 generates the first obtained image based on the first obtained projection data. The image generation unit 33 generates the second obtained image based on the second obtained projection data. The image generation unit 33 outputs the generated first obtained image and second obtained image to the positional shift detection unit 35.

The positional shift detection unit 35 detects object projection images on the first and second obtained images in each same imaging direction in the first imaging and the second imaging. For example, the positional shift detection unit 35 uses pattern matching processing to detect an object projection image. The positional shift detection unit 35 detects a relative positional shift by using the projection images detected on the first and second obtained images in the same projection direction. The positional shift detection unit 35 outputs the detected relative positional shift to the positional shift correction unit 37.

(Positional Shift Correction Reconstruction Function)

Figure 4:
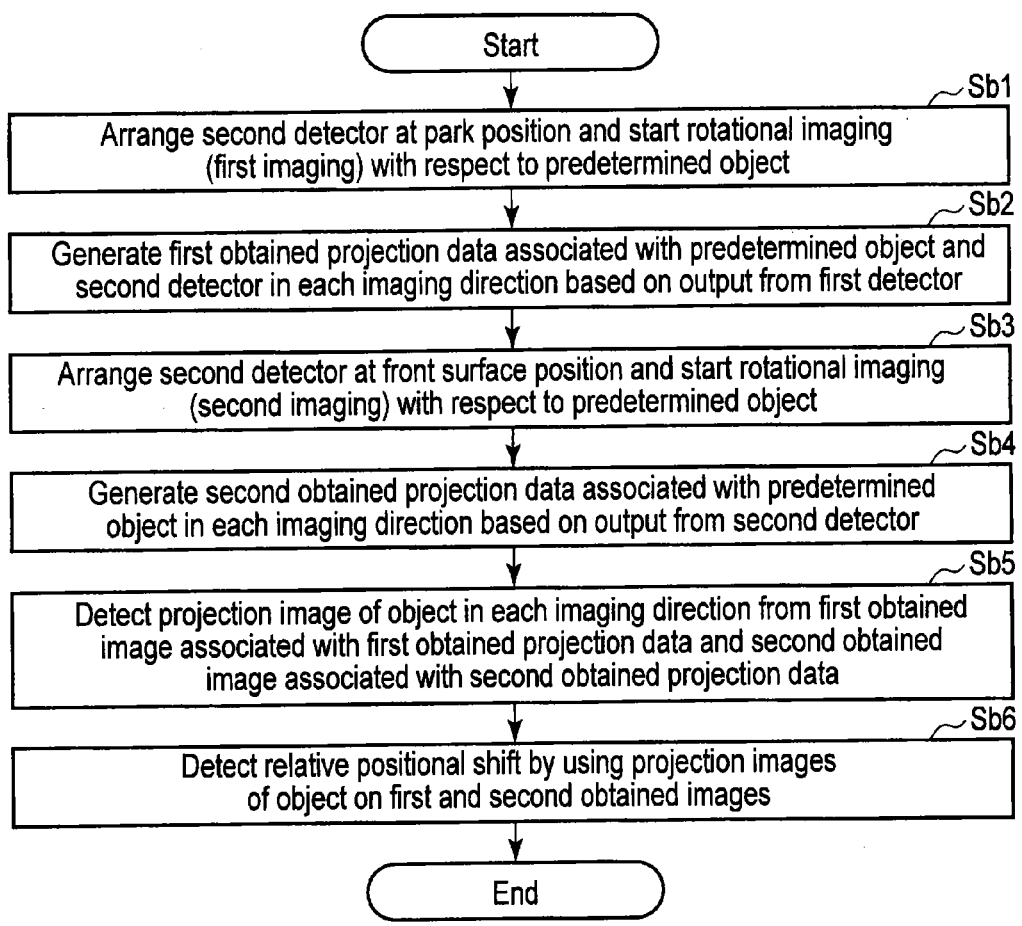
FIG. 4 is a flowchart showing an example of a procedure for positional shift correction reconstruction processing according to the first modification of the first embodiment.

FIG. 4 is a flowchart showing an example of a procedure for positional shift correction reconstruction processing according to this modification. In this positional shift correction reconstruction processing, the first imaging and the second imaging are executed before object imaging to detect the positional shift of the second detector 23 relative to the first detector 19.

The first correspondence table for correcting the orbit shift between the rotational orbit of the first detector 19 and the ideal rotational orbit is read out from the storage unit 43. The first correspondence table is generated before the detection of the positional shift of the second detector 23 relative to the first detector 19. The second detector 23 is arranged at the park position, and the first imaging is executed for a predetermined object (step Sb1). The first obtained projection data associated with the predetermined object and the second detector 23 is generated in each imaging direction based on an output from the first detector 19 (step Sb2).

The second detector 23 is arranged in front of the first detector 19, and the second imaging is executed with respect to the same object (step Sb3). The second obtained projection data associated with the object is generated in each imaging direction based on an output from the second detector 23 (step Sb4). The first obtained image is generated based on the first obtained projection data. The second obtained image is generated based on the second obtained projection data. An object projection image is detected in each imaging direction from the first and second obtained images (step Sb5).

A relative positional shift is detected in each imaging direction by using object projection images in the first and second obtained images in the same imaging direction (step Sb6). The origin moving vector $V_\phi$ and the rotation matrix $R_\phi$ are calculated in each imaging direction $\phi$ based on the relative positional shift. The second correspondence table for correcting the relative positional shift in each imaging direction is generated based on the origin moving vector $V_{100}$ and the rotation matrix $R_\phi$.

Rotational imaging (object imaging) is executed with respect to the object. The second projection data is generated in each imaging direction based on an output from the second detector second detector 23. Corrected projection data is generated by correcting the second projection data based on the first and second correspondence tables. Volume data is reconstructed based on the correction projection data.

(Second Modification)

A difference from the first embodiment is that the second correspondence table is generated at the time of imaging an object.

The second detector 23 preferably has a structure which enables as many X-rays transmitted through the second detector 23 as possible to reach the first detector 19, in order to improve the marker detection efficiency of the first detector 19. For example, the second detector 23 has a structure in which unnecessary radiopaque components (e.g., a power supply circuit and a lead shield) are not provided on the rear surface of the second detection surface.

The imaging control unit 29 executes object imaging by using the second detector 23 arranged at the front surface position after the generation of the first correspondence table. When using an image sensor end of the second detector 23 as a landmark, the imaging control unit 29 may control the beam limiting device 17 to irradiate a region covering the second detection surface and slightly wider than the second detection surface with X-rays.

At this time, the beam limiting device 17 limits an irradiation range to irradiate the region covering the second detection surface and slightly wider than the second detection surface with X-rays. More specifically, the beam limiting device 17 limits an irradiation range by moving the first and second collimator blades under the control of the imaging control unit 29 in object imaging.

The projection data generation unit 31 generates the first projection data based on an output from the first detector 19 in object imaging. The projection data generation unit 31 generates the second projection data based on an output from the second detector 23 in object imaging. The projection data generation unit 31 outputs the first projection data to the image generation unit 33. The projection data generation unit 31 outputs the second projection data to the positional shift correction unit 37.

The positional shift detection unit 35 detects the positional shift of the second detector 23 relative to the first detector 19 in rotational imaging in accordance with an imaging direction by using the first projection data and a predetermined positional relationship in each imaging direction in object imaging. Note that the method of detecting a relative positional shift is not limited to that described above, and the method described in the first embodiment or the first modification may be used.

The positional shift correction unit 37 corrects the second projection data associated with object imaging by using the first and second correspondence tables.

The reconstruction unit 39 reconstructs volume data by using the corrected second projection data (corrected projection data).

(Positional Shift Correction Reconstruction Function)

Figure 5:
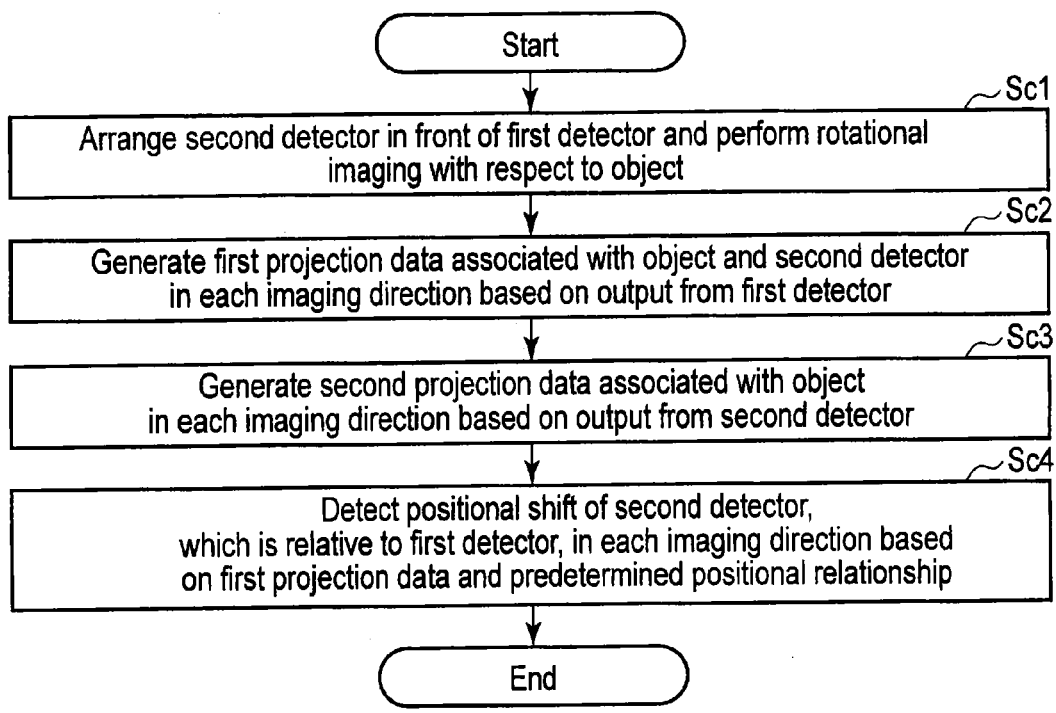
FIG. 5 is a flowchart showing an example of a procedure for positional shift correction reconstruction processing according to the second modification of the first embodiment.

FIG. 5 is a flowchart showing an example of a procedure for positional shift correction reconstruction processing according to this modification. In this positional shift correction reconstruction processing, object imaging is performed after the generation of the first correspondence table to detect the positional shift of the second detector 23 relative to the first detector 19.

The first correspondence table for correcting the orbit shift between the rotational orbit of the first detector 19 and the ideal rotational orbit and a predetermined positional relationship are read out from the storage unit 43. The second detector 23 is arranged in front of the first detector 19, and rotational imaging (object imaging) is performed with respect to an object along an orbit around the rotation axis (step Sc1).

At this time, an irradiation range is limited to irradiate a region covering the second detection surface and slightly larger than the second detection surface with X-rays. The first projection data associated with the object and the second detector 23 is generated in each imaging direction based on an output from the first detector 19 (step Sc2). The second projection data associated with the object is generated in each imaging direction based on an output from the second detector 23 (step Sc3).

The positional shift of the second detector 23 relative to the first detector 19 is detected in each imaging direction based on the first projection data and the predetermined positional relationship (step Sc4). Note that the positional shift of the second detector 23 relative to the first detector 19 may be detected in each imaging direction based on the first projection data and the second projection data.

The origin moving vector $V_\phi$ and the rotation matrix $R_\phi$ are calculated in each imaging direction $\phi$ based on the relative positional shift. The second correspondence table for correcting the relative positional shift in each imaging direction is generated based on the origin moving vector $V_\phi$ and the rotation matrix $R_\phi$. Corrected projection data is generated by correcting the second projection data by using the first and second correspondence tables. Volume data is reconstructed based on the corrected projection data.

According to the above arrangement, the following effects can be obtained.

The X-ray diagnostic apparatus 1 according to this embodiment can detect the positional shift of the second detector 23 relative to the first detector 19 by arranging the second detector 23 having markers (indicator points) provided on its rear surface in front of the first detector 19, and imaging the second detector 23 by using the first detector 19 in associate with rotational imaging. The X-ray diagnostic apparatus 1 then can generate the second correspondence table for correcting the positional shift of the second projection data based on the relative positional shift. This enables the X-ray diagnostic apparatus 1 to correct the second projection data by using the first and second correspondence tables for correcting the orbit shift between the rotational orbit of the first detector 19 and the ideal rotation orbit in rotational imaging and reconstruct volume data based on the corrected second projection data.

For these reasons, the X-ray diagnostic apparatus 1 according to this embodiment can generate a table (second correspondence table) associated with the correction of the geometrical deformation, displacement, and vibration characteristics of the C-arm including the holder mechanism for the MAF detector (second detector 23). According to the X-ray diagnostic apparatus 1 of the embodiment, therefore, it is possible to reduce the manufacturing cost, improve the serviceability, and reconstruct volume data with higher accuracy by correcting the positional shift of projection data caused by the geometrical deformation and vibration of the C-arm (support arm 13) in a shorter time.

In addition, the X-ray diagnostic apparatus 1 according to the first modification of this embodiment can generate the second correspondence table without providing any marker on the rear surface of the second detector 23. This can further reduce the cost. Furthermore, the X-ray diagnostic apparatus 1 according to this modification can correct the geometrical deformation, displacement, and vibration characteristics of the C-arm including the holder mechanism for the MAF detector (second detector 23) even in the MAF system without any markers.

In addition, the X-ray diagnostic apparatus 1 according to the second modification of this embodiment can generate the second correspondence table by rotational imaging for an object. This makes it possible to generate the second correspondence table concurrently with object imaging and hence to correct the geometrical deformation, displacement, and vibration characteristics of the C-arm including the holder mechanism which slightly wobbles in every object imaging. It is therefore possible to reconstruct volume data with higher accuracy.

In addition, the X-ray diagnostic apparatus 1 according to the second modification of this embodiment need not perform pre-calibration processing for the second detector 23, and improves the serviceability for the operator. Furthermore, the X-ray diagnostic apparatus 1 can correct a relative positional shift without undergoing a change in mechanical characteristics (including not only a temporal change but also a change upon, for example, the detachment of the second detector 23 from the support mechanism 21 for maintenance, repair, and the like).

That is, the X-ray diagnostic apparatus 1 according to the second modification of this embodiment need not consider any shift in pre-calibration itself caused by a change in mechanical characteristics, and hence can maintain the correction accuracy of relative positional shifts constant. In addition, according to the X-ray diagnostic apparatus 1, it is possible to correct a relative positional shift in every imaging for an object, and hence accurate repeatability is not required concerning the position of the second detector 23 arranged at the front surface position. This can alleviate the requirement for high mechanical accuracy with respect to the support mechanism 21. This can further reduce the manufacturing cost of the X-ray diagnostic apparatus 1.

In addition, each function according to this embodiment and these modifications can be implemented by installing programs (medical image processing programs) for executing positional shift detection processing, positional shift correction processing, positional shift correction reconstruction processing, and the like in the computer of the X-ray diagnostic apparatus 1 and loading them to the memory. In this case, the programs which can cause the computer to execute this method can be distributed by being stored in storage media such as magnetic disks (floppy disks, hard disks, and the like), optical disks (CD-ROMs, DVDs, and the like), and semiconductor memories.

(Second Embodiment)

A difference from the first embodiment is that at least one of the position of a collimator blade and the position of a compensation filter is corrected in accordance with an imaging direction based on the positional shift of a second detector 23 relative to a first detector 19.

An input unit 41 inputs an instruction to execute a collimator control mode of correcting the position of the collimator blade in accordance with an imaging direction. Note that the input unit 41 may input an instruction to execute a compensation filter control mode of correcting the position of the compensation filter in accordance with an imaging direction. The input unit 41 inputs an imaging direction with respect to an object P upon inputting in the above mode.

A positional shift correction unit 37 decides a positional shift correction amount for the second detector 23 by using the second correspondence table in accordance with an imaging direction in response to the inputting of the collimator control mode or compensation filter control mode. A positional shift correction amount ($V_\phi$, $\theta_\phi$) in the second correspondence table is calculated by an arbitrary method described in the first embodiment. The positional shift correction unit 37 decides a blade position correction amount for the correction of an aperture blade position based on the decided positional shift correction amount.

Note that the positional shift correction unit 37 may decide a filter position correction amount for the correction of the position of the compensation filter which attenuates an X-ray dose based on the decided positional shift correction amount in response to the inputting of the compensation filter control mode. The positional shift correction unit 37 outputs the blade position correction amount and the filter position correction amount to an imaging control unit 29.

For the sake of simplicity, the collimator control mode and a blade position correction amount will be described below. When inputting the compensation filter control mode, the position of the collimator blade and the blade position correction amount in the following description should read as the position of the compensation filter and the filter position correction amount, respectively.

The positional shift correction unit 37 calculates a blade position correction amount from the positional shift correction amount ($V_\phi$, $\theta_\phi$) calculated in the first embodiment, a distance $SID_1$ between the first detector 19 and the radiation source and a distance (to be referred to as $SID_c$ hereinafter) between the collimator blade and the radiation source. More specifically, the positional shift correction unit 37 reads out a reduction ratio H(x, y) for the reflection of the positional shift correction amount in the position of the collimator blade from a storage unit 43. The reduction ratio H(x, y) is calculated as the ratio of $SID_c(x, y)$ to $SID_1(x, y)$ (H(x, y)=$SID_c(x, y)/SID_1(x, y)$). The positional shift correction unit 37 calculates a blade position correction amount ($V_{\phi c}$, $\theta_{\phi c}$) in a plane covering the collimator blade by correcting the positional shift correction amount ($V_\phi$, $\theta_\phi$) using the reduction ratio H(x, y).

The imaging control unit 29 controls an irradiation field limiting device 17 to move the collimator blade based on the blade position correction amount. Note that the imaging control unit 29 may control the irradiation field limiting device 17 by moving the compensation filter based on the filter position correction amount. In addition, the imaging control unit 29 rotates a support arm 13 in accordance with the imaging direction input by the operator.

The irradiation field limiting device 17 moves the collimator blade in accordance with the blade position correction amount under the control of the imaging control unit 29. The irradiation field limiting device 17 includes at least one compensation filter to be inserted into an X-ray irradiation field to reduce the exposure dose of the object and improve image quality. The compensation filter is made of, for example, aluminum or copper. The compensation filter is inserted into the X-ray irradiation field of the irradiation field limiting device 17 under the control of the imaging control unit 29. For example, the compensation filter is used to prevent halation. The irradiation field limiting device 17 moves the compensation filter in accordance with a filter position correction amount under the control of the imaging control unit 29.

Figure 6:
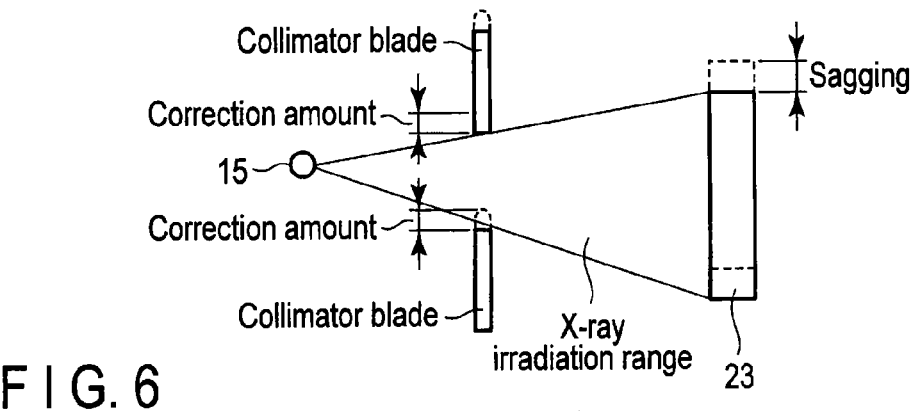
FIG. 6 is a view showing the positional shift (sagging) of a second detector 23 in an imaging direction of 90°, with the imaging angle at which an object is imaged from the rear surface of the top plate being 0°, and the correction of the position of a collimator blade in accordance with the positional shift of the second detector 23 according to the second embodiment.

FIG. 6 is a view showing the positional shift (sagging) of the second detector 23 in an imaging direction of 90°, with the imaging angle at which an object is imaged from the rear surface of the top plate being 0°, and the correction of the position of the collimator blade in accordance with the positional shift of the second detector 23. As shown in FIG. 6, the position of the collimator blade is corrected in accordance with the positional shift of the second detector 23 and an imaging direction (angle).

(Blade Position Correction Function)

The blade position correction function is a function of moving the collimator blade in accordance with the blade position correction amount decided in accordance with the positional shift of the second detector 23 and an imaging direction. Processing (to be referred to as blade position correction processing hereinafter) associated with the blade position correction function will be described below. Note that when performing blade position correction processing associated with this modification, it is possible to correct the position of the compensation filter instead of the position of the collimator blade. In addition, it is possible to correct both the position of the collimator blade and the position of the compensation filter.

Figure 7:
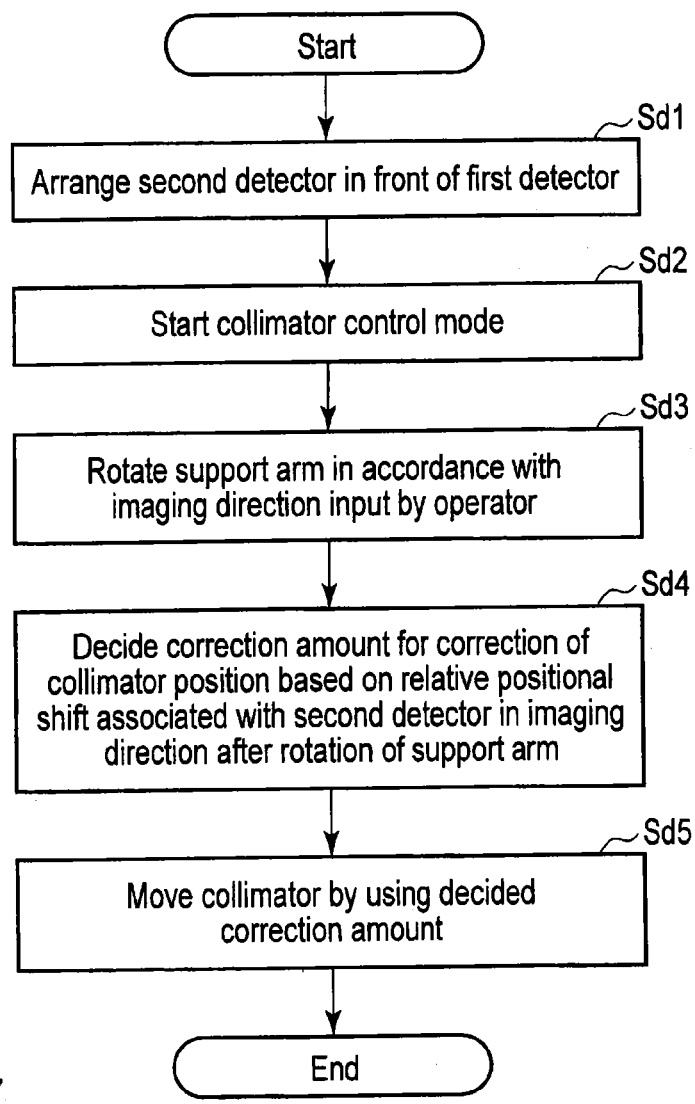
FIG. 7 is a flowchart showing an example of a procedure for blade position correction processing according to the second embodiment.

FIG. 7 is a view showing an example of a procedure for blade position correction processing according to this embodiment.

The second detector 23 is arranged in front of the first detector 19 (step Sd1). An instruction to input the collimator control mode is input via the input unit 41. The collimator control mode is started in response to the instruction to input the collimator control mode (step Sd2). The support arm 13 is rotated in accordance with the imaging direction input by the operator. A correction amount for the correction of the position of the collimator (blade position correction amount) is decided based on the relative positional shift of the second detector 23 in an imaging direction after the rotation of the support arm 13 (step Sd4). The collimator is moved by using the decided correction amount (step Sd5).

Note that when an instruction to execute the compensation filter control mode is input, the compensation filter control mode is started in step Sd2. In addition, in step Sd4, a filter position correction amount is decided based on the relative positional shift of the second detector 23 in an imaging direction after the rotation of the support arm 13. The compensation filter is moved by using the decided correction amount.

According to the above arrangement, the following effects can be obtained.

An X-ray diagnostic apparatus 1 according to this embodiment can decide correction amounts for the correction of the position of the collimator and the position of the compensation filter (a blade position correction amount and a filter position correction amount) in accordance with an imaging direction based on the positional shift of the second detector 23 relative to the first detector 19. The X-ray diagnostic apparatus 1 can then move the collimator blade or compensation filter by using the decided correction amount. For these reasons, the X-ray diagnostic apparatus 1 can always properly execute collimation with respect to the second detector 23, as shown in FIG. 6. This makes it possible to prevent an object from being unnecessarily exposed to X-rays. In addition, it is possible to prevent interference with image observation caused by collimation (focusing) unintended by the operator. When the rotational angle of the support arm 13 with respect to the vertical axis is large, in particular, the irradiation range of X-rays is made proper, and the detection surface of the second detector 23 can be effectively used.

In addition, each function according to this embodiment can be implemented by installing programs (blade position correction programs) for executing positional shift detection processing, blade position correction processing, and the like in the computer of the X-ray diagnostic apparatus 1 and loading them to the memory. In this case, the programs which can cause the computer to execute this method can be distributed by being stored in storage media such as magnetic disks (floppy® disks, hard disks, and the like), optical disks (CD-ROMs, DVDs, and the like), and semiconductor memories.

(Third Embodiment)

A difference from the first and second embodiments is that the projection direction in which three-dimensional image data is projected is corrected based on the positional shift of a second detector 23 relative to a first detector 19, and the third projection data is generated by projecting the three-dimensional image data in the corrected projection direction.

An interface unit 3 receives the three-dimensional image data generated in advance by various types of medical image diagnostic apparatuses via a network. The interface unit 3 outputs the three-dimensional image data to a storage unit 43. The various types of medical image diagnostic apparatuses include, for example, an X-ray CT (Computed Tomography) apparatus, an MRI (Magnetic Resonance Imaging) apparatus, an X-ray diagnostic apparatus, and a nuclear medicine diagnostic apparatus.

An imaging control unit 29 outputs the geometrical position (to be referred to as geometrical information hereinafter) of a support arm 13 at the time of acquisition of the second projection data to a positional shift correction unit 37. The geometrical information is, for example, an imaging direction at the time of acquisition of the second projection data.

The storage unit 43 stores three-dimensional image data associated with an object. The three-dimensional image data is the volume data acquired in advance by various types of medical image diagnostic apparatuses. The three-dimensional image data includes, for example, data on which a CT image, an MRI image, a three-dimensional blood vessel image, and the like are based.

The positional shift correction unit 37 corrects a positional shift in the projection direction in which three-dimensional image data is projected, based on an imaging direction associated with the second projection data associated with an object and a relative positional shift. A correction amount ($V_\varphi$, $\theta_\varphi$) associated with a relative positional shift is calculated by an arbitrary method described in the first embodiment. The positional shift correction unit 37 outputs the corrected projection direction to a projection data generation unit 31. Note that the positional shift correction unit 37 may output the corrected projection direction to an image generation unit 33.

The projection data generation unit 31 generates the third projection data by projecting the three-dimensional image data along the corrected projection direction. The projection data generation unit 31 executes projection of the three-dimensional image data along the corrected projection direction by, for example, a predetermined computer simulation. The projection data generation unit 31 outputs the third projection data to the image generation unit 33. The third projection data is, for example, blood vessel projection data or X-ray-like projection data. When the angle of the support arm 13 is 0° or 180° with reference to the vertical direction, that is, the second detector 23 is located immediately above or below the top plate, the projection data generation unit 31 generates the third projection data by projecting the three-dimensional image data along a projection direction of 0° or 180°.

The image generation unit 33 generates a superimposed image by superimposing the third projection data on the second projection data. Note that the image generation unit 33 may generate a superimposed image by generating the third image based on the third projection data and superimposing the third image on the second image. The image generation unit 33 outputs the superimposed image to a display unit 45. The third image is, for example, a blood vessel image or X-ray-like image. Note that the image generation unit 33 may generate the third image by performing rendering processing using a corrected projection direction.

The display unit 45 displays the superimposed image.

An input unit 41 inputs an instruction associated with the execution of correction in a projection direction. This instruction is, for example, an instruction to input a 3D road map mode.

FIG. 8 is an example of a 3D road map image obtained by superimposing the third image generated by using a corrected projection direction on the second image. FIG. 8 shows a state in which the second detector 23 moved in front of the first detector 19 is arranged at a side surface (e.g., the 90° front position) of an object P (top plate). At this time, the positional shift correction unit 37 corrects the projection direction in which volume data is projected, by using a positional shift corresponding to the sagging of the second detector 23 (the positional shift of the second detector 23 relative to the first detector 19). With this correction, the X-ray irradiation range associated with the second projection data acquired by the second detector 23 coincides with the virtual X-ray irradiation range associated with the third projection data generated from three-dimensional image data by using the corrected projection direction.

That is, as shown in FIG. 8, the second image generated from the second projection data coincides with the third image generated from the third projection data in terms of positional relationship. Therefore, the 3D road map image obtained by superimposing the third image on the second image is displayed without any positional shift between the second image and the third image.

(Projection Direction Correction Function)

The projection direction correction function is a function of generating the third projection data by correcting a positional shift in the projection direction in which three-dimensional image data is projected by using geometrical information and a relative positional shift, and projecting the three-dimensional image data in the corrected projection direction. Processing associated with the projection direction correction function (to be referred to as projection direction correction processing hereinafter) will be described below. For the sake of simplicity, assume that a superimposed image is a 3D road map image.

FIG. 9 is a flowchart showing an example of a procedure for projection direction correction processing.

The second detector 23 is arranged in front of the first detector 19 (step Se1). The 3D road map mode is started in accordance with the instruction issued by the operator via the input unit 41 (step Se2). In addition, three-dimensional image data to be used in the 3D road map mode is selected in accordance with the selection instruction issued by the operator via the input unit 41. The support arm 13 rotates in accordance with the imaging direction input by the operator via the input unit 41 (step Se3). The second detector 23 detects the X-rays transmitted through the object P. The second projection data is generated based on an output from the second detector 23.

The projection direction in which three-dimensional image data is projected is corrected based on the positional shift of the second detector 23 relative to the first detector 19 (step Se4). The third projection data is generated by projecting the three-dimensional image data along the corrected projection direction (step Se5). A superimposed image (3D road map image) is generated by superimposing the third projection data on the second projection data (step Se6). The superimposed image (3D road map image) is displayed on the display unit 45 (step Se7). In the flowchart shown in FIG. 9, if the imaging direction is 0° or 180°, the processing in step Se4 may be omitted. In this case, in the processing in step Se5, the third projection data is generated by projecting three-dimensional image data along the defined imaging direction.

According to the above arrangement, the following effects can be obtained.

An X-ray diagnostic apparatus 1 according to this embodiment can correct the projection direction in which three-dimensional image data is projected, by using the positional shift of the second detector 23 relative to the first detector 19. That is, the X-ray diagnostic apparatus 1 can correct the virtual X-ray irradiation range associated with the third projection data in accordance with an X-ray irradiation range caused by the displacement (relative positional shift) of the second detector 23 due to gravity, as shown in FIG. 8. With this operation, the X-ray diagnostic apparatus 1 can prevent a positional shift between the third projection data (third image) obtained by projecting the three-dimensional image data in the corrected projection direction and the second projection data (second image).

In addition, each function according to this embodiment can be implemented by installing programs (projection direction correction programs) for executing positional shift detection processing, projection direction correction processing, and the like in the computer of the X-ray diagnostic apparatus 1 and loading them to the memory. In this case, the programs which can cause the computer to execute this method can be distributed by being stored in storage media such as magnetic disks (floppy disks, hard disks, and the like), optical disks (CD-ROMs, DVDs, and the like), and semiconductor memories.

(Fourth Embodiment)

A difference from the first to third embodiments is that a counterweight is provided to compensate for the difference in the barycentric position (to be referred to as the barycentric difference hereinafter) of the second detector 23 with respect to the support arm 13 between the first state in which the second detector 23 is arranged at the park position and the second state in which the second detector 23 is arranged at the front surface position.

Figure 10:
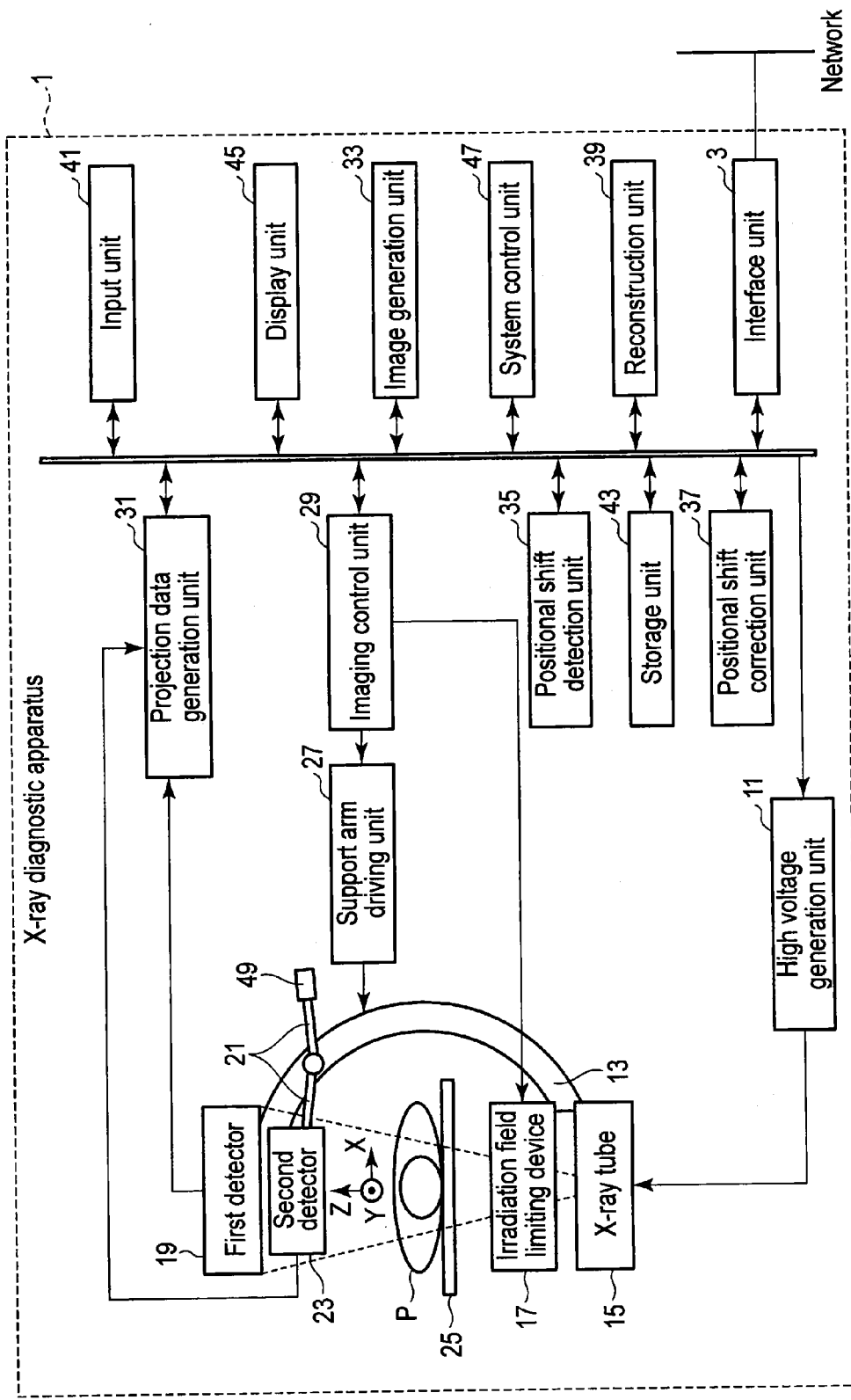
FIG. 10 is a block diagram showing the arrangement of an X-ray diagnostic apparatus according to the fourth embodiment.

FIG. 10 shows the arrangement of an X-ray diagnostic apparatus 1 according to the fourth embodiment.

A counterweight 49 compensates for the difference in the barycentric position of the second detector 23 between the first state in which a second detector 23 is retracted from the X-ray irradiation range associated with a first detector 19 and the second state in which the second detector 23 is arranged in front of the first detector 19. The counterweight 49 has a point-like shape or rod-like shape. The counterweight 49 has a weight which makes the difference in barycentric position, that is, the barycentric distribution in the first state and the barycentric distribution in the second state, almost invariable. When the distance from a connecting portion between the support mechanism 21 and a support arm 13 to the center of gravity of the second detector 23 is almost equal to the distance from the connecting portion to the center of gravity of the counterweight 49, the counterweight 49 has a weight almost equal to the second detector 23.

A support mechanism 21 supports the counterweight 49 so as to enable it to compensate for the barycentric difference in accordance with the first and second states. The support mechanism 21 supports the counterweight 49 so as to be located on one side or two sides of the first detector 19. Note that the support mechanism 21 may support the counterweight 49 so as to surround the first detector 19. The support mechanism 21 movably supports the counterweight 49 and the second detector 23. More specifically, the support mechanism 21 supports the counterweight 49 so as to allow it to move in a direction opposite to the moving direction of the second detector between the first and second states.

For example, when moving the second detector 23 from the front surface position to the park position, the support mechanism 21 moves the counterweight 49 from the park position to the front surface position. In addition, when moving the second detector 23 from the park position to the front surface position, the support mechanism 21 moves the counterweight 49 from the front surface position to the park position. That is, when the second detector 23 is arranged at the park position, the support mechanism 21 arranges the counterweight 49 at a position near the front surface position so as to compensate for the barycentric difference. When the second detector 23 is arranged at the front surface position, the support mechanism 21 arranges the counterweight 49 at the park position.

Figure 11:
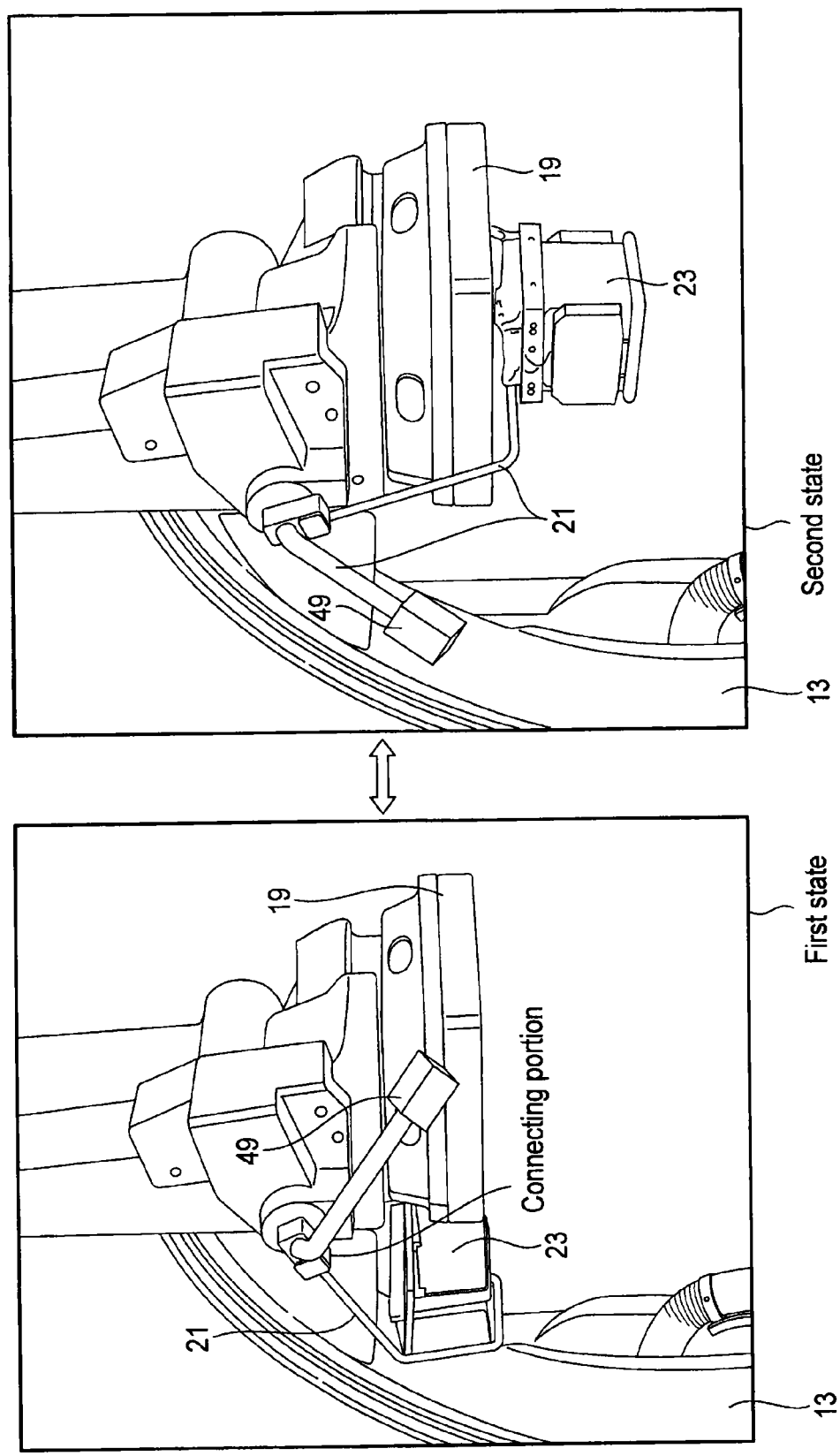
FIG. 11 is a view showing a point-like counterweight in the first state in which the second detector is arranged at the park position and the point-like counterweight in the second state in which the second detector is arranged at the front surface position according to the fourth embodiment.

FIG. 11 is a view showing the point-shaped counter 49 in the first state in which the second detector 23 is arranged at the park position, and the point-shaped counterweight 49 in the second state in which the second detector 23 is arranged at the front surface position. As shown on the left side of FIG. 11, the point-shaped counterweight 49 in the first state is arranged near the front surface position. As shown on the right side of FIG. 11, the point-shaped counterweight 49 in the second state is arranged at the park position.

Figure 12:
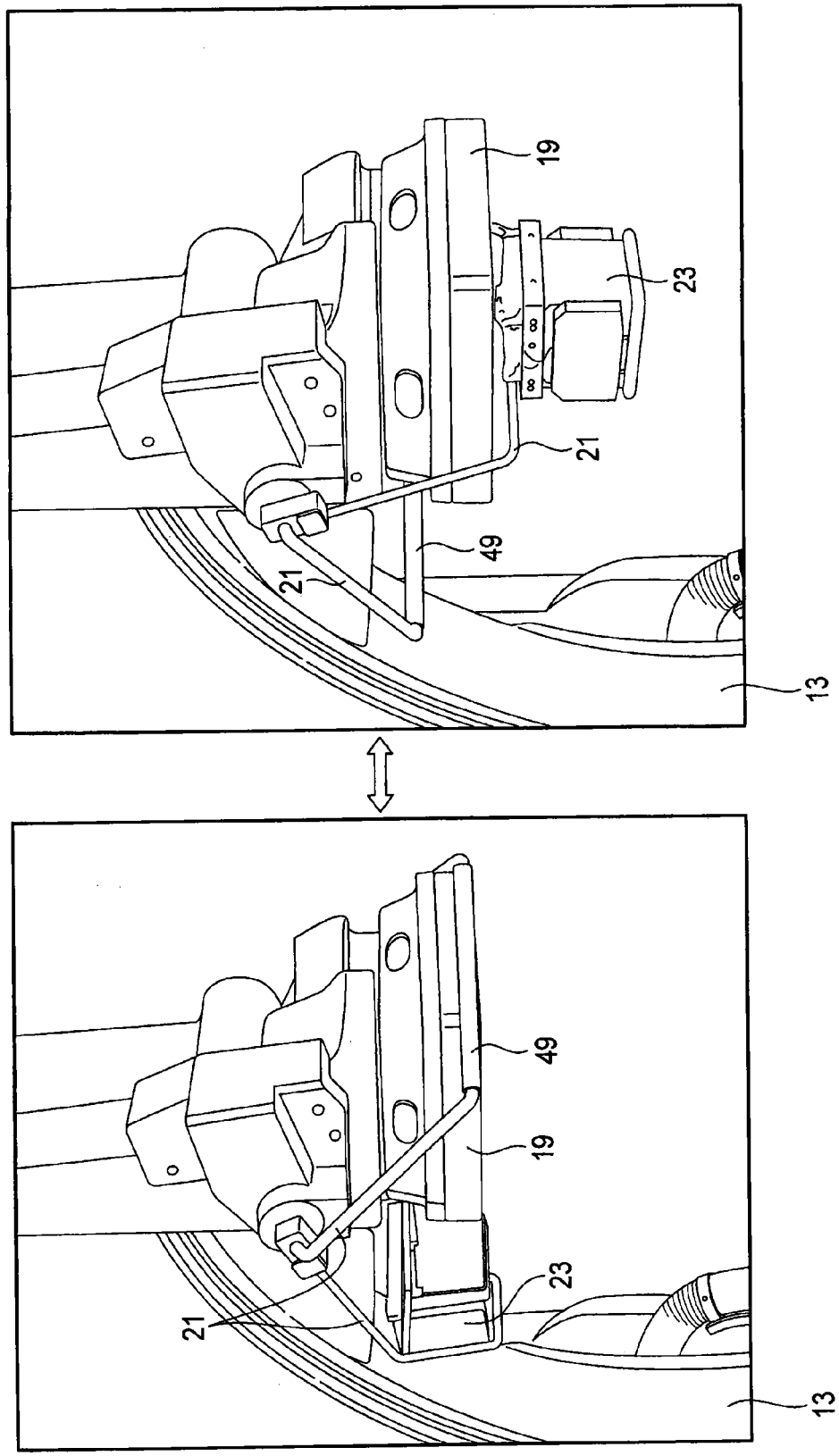
FIG. 12 is a view showing a rod-like counterweight in the first state in which the second detector is arranged at the park position and the rod-like counterweight in the second state in which the second detector is arranged at the front surface position according to the fourth embodiment.
Figure 13:
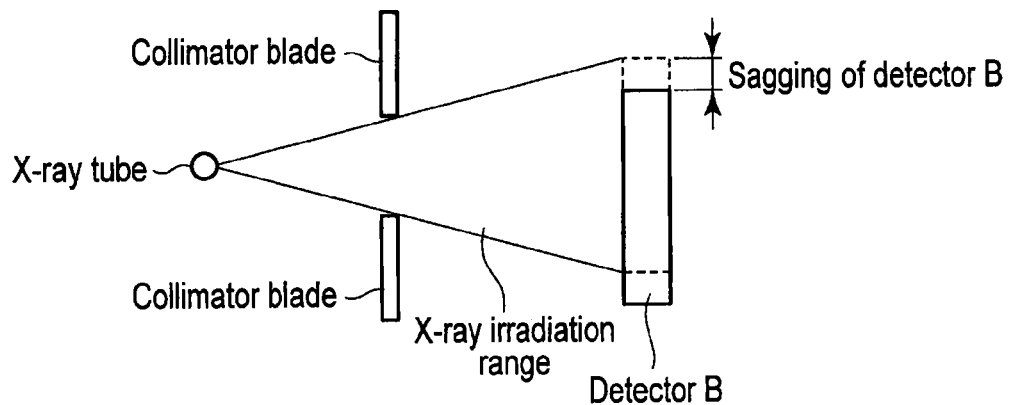
FIG. 13 is a view showing the position of a collimator blade and the sagging of detector B when the angle of a C-arm is 90° according to a related art.
Figure 14:
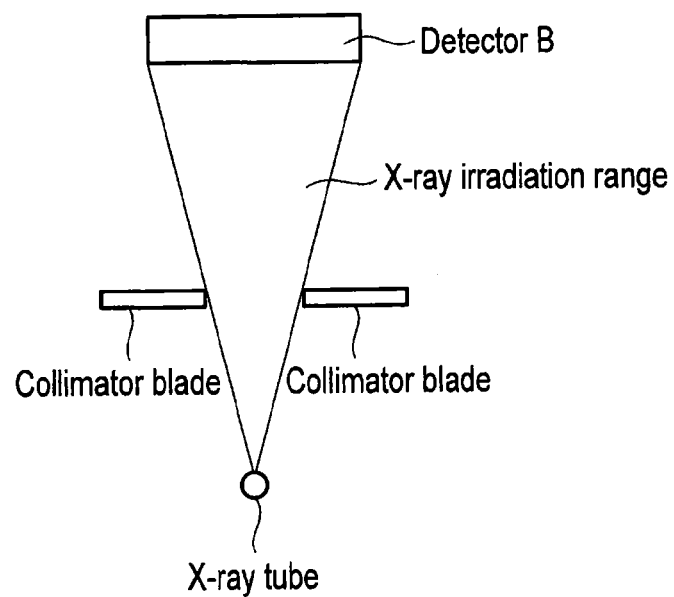
FIG. 14 is a view showing the position of the collimator blade and detector B when the angle of the C-arm is 0° according to the related art.
Figure 15:
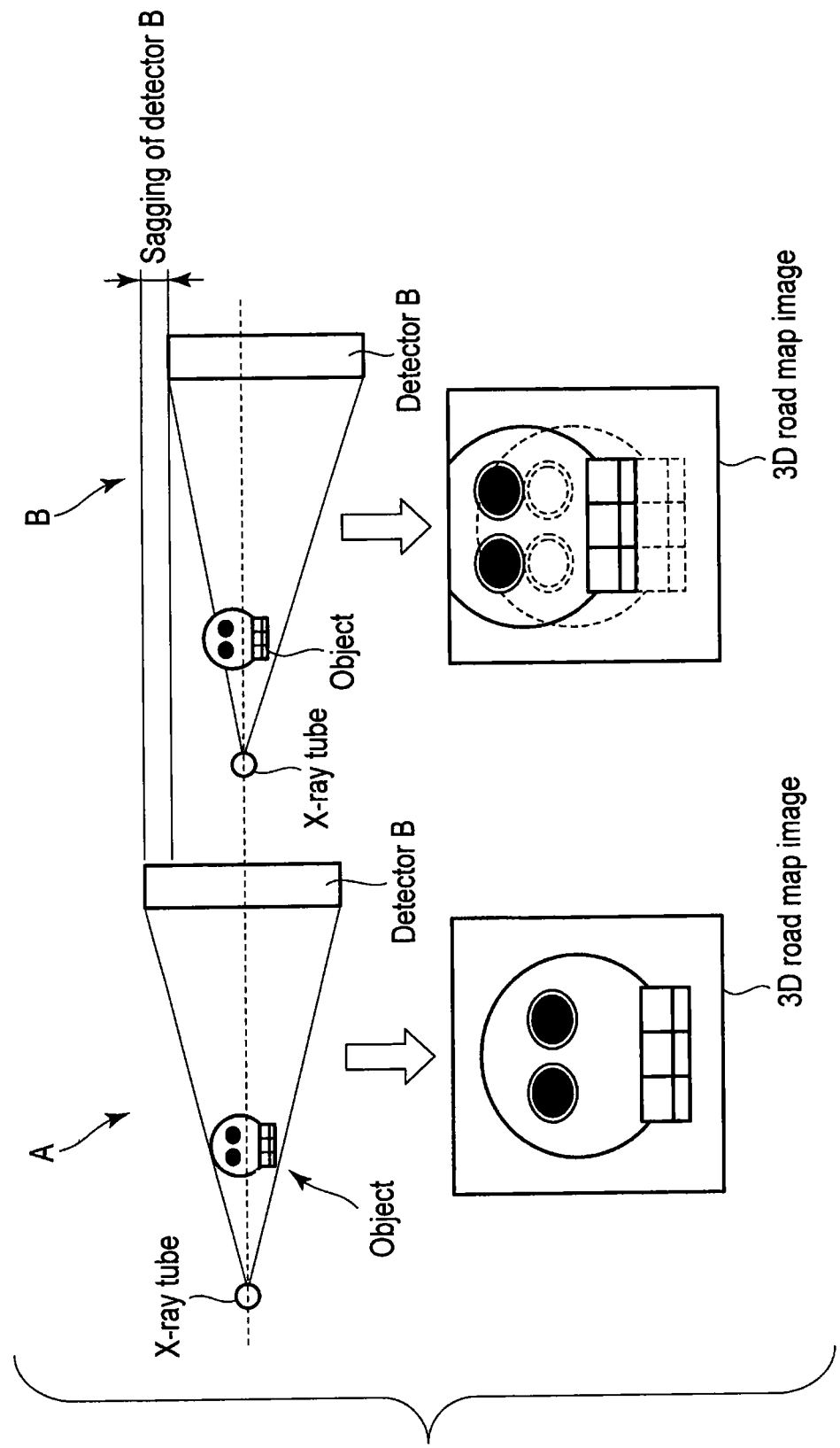
FIG. 15 is a view showing that an X-ray irradiation range differs from an ideal irradiation range because of the sagging of detector B according to the related art.

FIG. 12 is a view showing the rod-shaped counterweight 49 in the first state in which the second detector 23 is arranged at the park position, and the rod-shaped counterweight 49 in the second state in which the second detector 23 is arranged at the front surface position. As shown on the left side of FIG. 12, the rod-like counterweight 49 in the first state is arranged near the front surface position. As shown on the right side of FIG. 12, the rod-shaped counterweight 49 in the second state is arranged at the park position.

According to the above arrangement, the following effects can be obtained.

The X-ray diagnostic apparatus 1 according to this embodiment can be provided with the counterweight 49 for compensating for the difference in the barycentric position of the second detector 23 with respect to the support arm 13 between the first state in which the second detector 23 is arranged at the park position and the second state in which the second detector 23 is arranged at the front surface position. With this arrangement, the X-ray diagnostic apparatus 1 according to this embodiment can suppress and reduce a change in the vibration characteristics of the support arm 13 in rotational imaging. That is, according to this embodiment, it is possible to keep the vibration characteristics of the support arm 13 almost constant in rotational imaging.

As described above, according to this embodiment, the correction accuracy of a relative positional shift is improved by improving the repeatability of the first correspondence table associated with the first detector 19.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:
   an X-ray tube configured to generate X-rays;
   a first detector configured to detect the X-rays;
   at least one second detector arranged in front of a first detection surface of the first detector and including a second detection surface narrower than the first detection surface and a plurality of indicator points provided on a rear surface of the second detection surface;

projection data generation circuitry configured to generate first projection data based on an output from the first detector; and positional shift detection circuitry configured to detect a positional shift of the second detector relative to the first detector in accordance with an imaging direction by using the first projection data and a predetermined positional relationship between the indicator points and a plurality of detection elements in the second detector.

2. The apparatus according to claim 1, wherein the projection data generation circuitry is further configured to generate the first projection data in association with rotational imaging of performing imaging while rotating, along a predetermined orbit around a predetermined rotation axis, the X-ray tube, the first detector, and the second detector, and to generate second projection data based on an output from the second detector in association with the rotational imaging with respect to an object, and the apparatus further comprises positional shift correction circuitry configured to correct the positional shift of the second projection data by using the imaging direction in the rotational imaging and the positional shift, and reconstruction circuitry configured to reconstruct volume data based on the corrected second projection data.

3. The apparatus according to claim 2, further comprising a memory to store a first correspondence table used for orbit correction of correcting an orbit shift of the first detector relative to the orbit in accordance with the imaging direction, wherein the positional shift correction circuitry is further configured to generate a second correspondence table used for correction of the positional shift with respect to the imaging direction, and to correct the second projection data by using the first correspondence table and the second correspondence table.

4. The apparatus according to claim 3, wherein the positional shift detection circuitry is further configured to detect the positional shift before the rotational imaging with respect to the object, and the positional shift correction circuitry is further configured to generate the second correspondence table before the rotational imaging with respect to the object.

5. The apparatus according to claim 3, wherein the positional shift detection circuitry is further configured to detect the positional shift during the rotational imaging, and the positional shift correction circuitry is further configured to generate the second correspondence table based on the detected positional shift.

6. The apparatus according to claim 3, wherein the second projection data is projection data obtained in a predetermined imaging direction different from the imaging direction in the second correspondence table, the positional shift correction circuitry is further configured to interpolate a positional shift corresponding to the predetermined imaging direction by using two imaging directions adjacent to the predetermined imaging direction, the predetermined imaging direction, and the two positional shifts respectively corresponding to the two imaging directions in the second correspondence table, and to correct the second projection data by using the interpolated positional shift, and the reconstruction circuitry is further configured to reconstruct volume data based on the corrected second projection data.

7. The apparatus according to claim 2, wherein the rotational imaging is executed while maintaining a field of view covering a region which covers a detection surface of the second detector and is narrower than a detection surface of the first detector.

8. The apparatus according to claim 1, wherein the projection data generation circuitry is further configured to generate the first projection data in association with rotational imaging of imaging an object while rotating, along a predetermined orbit around a predetermined rotation axis, the X-ray tube, the first detector, and the second detector, and to generate second projection data based on an output from the second detector, and the apparatus further comprises positional shift correction circuitry configured to correct the second projection data by using the positional shift and the imaging direction in the rotational imaging, and reconstruction circuitry configured to reconstruct volume data based on the corrected second projection data.

9. The apparatus according to claim 1, further comprising image generation circuitry configured to generate an indicator point image including the indicator points based on the first projection data, wherein the positional shift detection circuitry is further configured to detect the indicator points on the indicator point image and to detect the positional shift by using the detected indicator points and the predetermined positional relationship.

10. The apparatus according to claim 9, wherein the indicator points are markers mounted on the second detector or structures forming the second detector, and the indicator points have a characteristic pattern including a transmitting region and a non-transmitting region with respect to the X-rays.

11. The apparatus according to claim 10, wherein a rear surface side of the indicator points is configured to transmit the X-rays.

12. The apparatus according to claim 9, wherein the positional shift detection circuitry is further configured to detect the positional shift by executing template matching or cross-correlation with respect to the indicator point image and a predetermined template image.

13. The apparatus according to claim 1, further comprising a counterweight configured to compensate for a difference in a barycentric position of the second detector between a first state in which the second detector is retracted from an X-ray irradiation range associated with the first detector and a second state in which the second detector is arranged in front of the first detector, and a support mechanism configured to movably support the counterweight and the second detector.

14. The apparatus according to claim 13, wherein the counterweight has a point-like shape, and the support mechanism is configured to support the counterweight so as to make the counterweight movable in a direction opposite to a moving direction of the second detector between the first state and the second state and so as to locate the counterweight on one side or two sides of the first detector.

15. The apparatus according to claim 13, wherein the counterweight has a rod-like shape, and the support mechanism is configured to support the counterweight so as to make the counterweight movable in a direction opposite to a moving direction of the second detector between the first state and the second state and so as to surround the first detector.

16. The apparatus according to claim 1, further comprising positional shift correction circuitry configured to correct a position of a collimator configured to limit an X-ray irradiation range or a positional shift of a compensation filter configured to attenuate a dose of the X-rays in accordance with the imaging direction.

17. The apparatus according to claim 1, further comprising positional shift correction circuitry configured to correct a positional shift in a projection direction in which three-dimensional image data acquired in advance is projected, based on the imaging direction and the positional shift.

18. The apparatus according to claim 17, wherein the three-dimensional image data is volume data acquired in advance by at least one of the X-ray diagnostic apparatus, an X-ray computed tomography apparatus, a magnetic resonance imaging apparatus, and a nuclear medical diagnostic apparatus.

19. The apparatus according to claim 18, wherein the projection data generation circuitry is further configured to generate second projection data based on an output from the second detector in association with rotational imaging of imaging an object while rotating, along a predetermined orbit around a predetermined rotation axis, the X-ray tube, the first detector, and the second detector, and to generate third projection data by projecting the three-dimensional image data along the corrected projection direction, and the apparatus further comprises a display to display a superimposed image obtained by superimposing the third projection data on the second projection data.

20. The apparatus according to claim 1, wherein the second detector has a higher spatial resolution than the first detector.

21. An X-ray diagnostic apparatus, comprising:
an X-ray tube configured to generate X-rays;
a first detector configured to detect the X-rays;
at least one second detector including a detection surface narrower than a detection surface of the first detector;
a support mechanism configured to support the second detector so as to make the second detector movable between a position at which the second detector is arranged in front of the detection surface of the first detector and a retraction position at which the second detector is retracted from a field of view associated with the first detector;
a support arm configured to support the X-ray tube, the first detector, and the support mechanism;
imaging control circuitry configured to execute first imaging of an object while arranging the second detector at the retraction position and rotating the support arm along a predetermined orbit around a predetermined rotation axis and to execute second imaging of the object while arranging the second detector in front of the detection surface of the first detector and rotating the second detector along the orbit around the rotation axis;
image generation circuitry configured to generate a first image based on an output from the first detector in the first imaging and to generate a second image based on an output from the second detector in the second imaging;
positional shift detection circuitry configured to detect a positional shift of the second detector relative to the first detector, in accordance with an imaging direction by detecting projection images of the object on the first image and on the second image; and
positional shift correction circuitry configured to correct a positional shift of the second image by using the positional shift corresponding to the imaging direction.

22. The apparatus according to claim 21, wherein the positional shift detection circuitry is further configured to detect the object by applying template matching or cross-correlation to the first image and the second image.

23. A medical image processing method, comprising:
storing first projection data obtained from a first detector;
storing second projection data obtained from a second detector and having a higher spatial resolution than the stored first projection data, and storing a projection image of at least one indicator point provided on a rear surface of the second detector;
detecting a positional shift of the second projection data relative to the first projection data, in accordance with an imaging direction by using the first projection data and a predetermined positional relationship between the at least one indicator point and a plurality of detection elements in the second detector;
correcting the second projection data by using the imaging direction and the positional shift; and
reconstructing volume data based on the corrected second projection data.

* * * * *